US008835375B2

(12) United States Patent
Haas et al.

(10) Patent No.: US 8,835,375 B2
(45) Date of Patent: Sep. 16, 2014

(54) CYCLIC ANGIOTENSIN ANALOGS

(75) Inventors: Marijke Haas, Groningen (NL); Leonardus Dorothea Kluskens, Groningen (NL); Anneke Kuipers, Haule (NL); Rick Rink, Groningen (NL); Sieger Adriaan Nelemans, Leens (NL); Gert Nikolaas Moll, Groningen (NL)

(73) Assignee: Applied Nanosystems B.V., Groningen (NL)

( * ) Notice: Subject to any disclaimer, the term of this patent is extended or adjusted under 35 U.S.C. 154(b) by 978 days.

(21) Appl. No.: 12/376,606

(22) PCT Filed: Aug. 7, 2007

(86) PCT No.: PCT/NL2007/050396

§ 371 (c)(1),
(2), (4) Date: Jul. 14, 2009

(87) PCT Pub. No.: WO2008/018792

PCT Pub. Date: Feb. 14, 2008

(65) Prior Publication Data

US 2010/0055146 A1 Mar. 4, 2010

(30) Foreign Application Priority Data

Aug. 8, 2006 (WO) ................ PCT/NL2006/000414

(51) Int. Cl.

| | |
|---|---|
| ***C07K 7/14*** | (2006.01) |
| ***A61K 38/00*** | (2006.01) |
| ***A61L 31/16*** | (2006.01) |

(52) U.S. Cl.

CPC . *C07K 7/14* (2013.01); *A61L 31/16* (2013.01); *A61L 2300/25* (2013.01)

USPC .......... 514/1.1; 514/16.3; 514/21.7; 530/316; 530/317; 530/328

(58) Field of Classification Search

None

See application file for complete search history.

(56) References Cited

U.S. PATENT DOCUMENTS

| | | | | |
|---|---|---|---|---|
| 6,028,168 A * | 2/2000 | Goodman et al. | ............ | 530/317 |
| 6,177,407 B1 * | 1/2001 | Rodgers et al. | .............. | 514/15.6 |

OTHER PUBLICATIONS

Ferrerira et al. Hypertension Sep. 2001.*

Zhang et al. J Med Chem 1996.*

* cited by examiner

*Primary Examiner* — James H Alstrum Acevedo

*Assistant Examiner* — Li Lee

(74) *Attorney, Agent, or Firm* — Hoffman & Baron, LLP

(57) ABSTRACT

The invention relates to analogs of angiotensins, in particular to cyclised analogs having Ang(1-8) agonistic or antagonistic activity and to cyclised Ang(1-7) analogs with agonistic or antagonistic activity and displaying improved proteolytic resistance compared to their linear counterparts. Provided is a cyclic angiotensin peptide analog comprising a thioether-bridge linkage between the amino acids corresponding to positions $Tyr^4$ and $Pro^7$ in naturally occurring Angiotensin. Also provided is the use of analogs in therapy, for example hypertension.

17 Claims, 11 Drawing Sheets

SEQUENCE LISTING

```
<160> NUMBER OF SEQ ID NOS: 30

<210> SEQ ID NO 1
<211> LENGTH: 8
<212> TYPE: PRT
<213> ORGANISM: Homo sapiens

<400> SEQUENCE: 1

Asp Arg Val Tyr Ile His Pro Phe
1               5


<210> SEQ ID NO 2
<211> LENGTH: 10
<212> TYPE: PRT
<213> ORGANISM: Homo sapiens

<400> SEQUENCE: 2

Asp Arg Val Tyr Ile His Pro Phe His Leu
1               5                   10


<210> SEQ ID NO 3
<211> LENGTH: 7
<212> TYPE: PRT
<213> ORGANISM: Homo sapiens

<400> SEQUENCE: 3

Arg Val Tyr Ile His Pro Phe
```

-continued

```
1               5


<210> SEQ ID NO 4
<211> LENGTH: 6
<212> TYPE: PRT
<213> ORGANISM: Homo sapiens

<400> SEQUENCE: 4

Val Tyr Ile His Pro Phe
1               5


<210> SEQ ID NO 5
<211> LENGTH: 10
<212> TYPE: PRT
<213> ORGANISM: Artificial
<220> FEATURE:
<223> OTHER INFORMATION: Cyclic angiotensin peptide analog (Xaa 1-10)
<220> FEATURE:
<221> NAME/KEY: MISC_FEATURE
<222> LOCATION: (1)..(1)
<223> OTHER INFORMATION: Xaa on position 1 is any amino acid, preferably
      a negatively charged amino acid, more preferably Asp
<220> FEATURE:
<221> NAME/KEY: MISC_FEATURE
<222> LOCATION: (2)..(2)
<223> OTHER INFORMATION: Xaa on position 2 is a positively charged amino
      acid, preferably Arg
<220> FEATURE:
<221> NAME/KEY: MISC_FEATURE
<222> LOCATION: (3)..(3)
<223> OTHER INFORMATION: Xaa on position 3 is an aliphatic amino acid,
      such as Ile, Val, Leu, preferably Val
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (5)..(5)
<223> OTHER INFORMATION: Xaa on position 5 is an aliphatic amino acid,
      such as Ile, Leu, Val, preferably Ile
<220> FEATURE:
<221> NAME/KEY: MISC_FEATURE
<222> LOCATION: (8)..(8)
<223> OTHER INFORMATION: Xaa on position 8 is other than Pro, preferably
      Phe
<220> FEATURE:
<221> NAME/KEY: MISC_FEATURE
<222> LOCATION: (9)..(9)
<223> OTHER INFORMATION: Xaa on position 9 is other than Pro, preferably
      His
<220> FEATURE:
<221> NAME/KEY: MISC_FEATURE
<222> LOCATION: (10)..(10)
<223> OTHER INFORMATION: Xaa on position 10 is an aliphatic amino acid,
      such as Ile, Leu, Val, preferably Leu

<400> SEQUENCE: 5

Xaa Xaa Xaa Tyr Xaa His Pro Xaa Xaa Xaa
1               5                   10


<210> SEQ ID NO 6
<211> LENGTH: 9
<212> TYPE: PRT
<213> ORGANISM: Artificial
<220> FEATURE:
<223> OTHER INFORMATION: Cyclic angiotensin peptide analog (Xaa 1-9)
<220> FEATURE:
<221> NAME/KEY: MISC_FEATURE
<222> LOCATION: (1)..(1)
<223> OTHER INFORMATION: Xaa on position 1 is any amino acid, preferably
      a negatively charged amino acid, more preferably Asp
<220> FEATURE:
<221> NAME/KEY: MISC_FEATURE
```

```
<222> LOCATION: (2)..(2)
<223> OTHER INFORMATION: Xaa on position 2 is a positively charged amino
      acid, preferably Arg
<220> FEATURE:
<221> NAME/KEY: MISC_FEATURE
<222> LOCATION: (3)..(3)
<223> OTHER INFORMATION: Xaa on position 3 is an aliphatic amino acid,
      such as Ile, Val, Leu, preferably Val
<220> FEATURE:
<221> NAME/KEY: MISC_FEATURE
<222> LOCATION: (4)..(7)
<223> OTHER INFORMATION: Position 4-7 is a thio-ether bridge
<220> FEATURE:
<221> NAME/KEY: MISC_FEATURE
<222> LOCATION: (5)..(5)
<223> OTHER INFORMATION: Xaa on position 5 is an aliphatic amino acid,
      such as Ile, Leu, Val, preferably Ile
<220> FEATURE:
<221> NAME/KEY: MISC_FEATURE
<222> LOCATION: (8)..(8)
<223> OTHER INFORMATION: Xaa on position 8 is other than Pro, preferably
      Phe
<220> FEATURE:
<221> NAME/KEY: MISC_FEATURE
<222> LOCATION: (9)..(9)
<223> OTHER INFORMATION: Xaa on position 9 is other than Pro, preferably
      His

<400> SEQUENCE: 6

Xaa Xaa Xaa Tyr Xaa His Pro Xaa Xaa
1               5


<210> SEQ ID NO 7
<211> LENGTH: 8
<212> TYPE: PRT
<213> ORGANISM: Artificial
<220> FEATURE:
<223> OTHER INFORMATION: Cyclic angiotensin peptide analog (Xaa 1-8)
<220> FEATURE:
<221> NAME/KEY: MISC_FEATURE
<222> LOCATION: (1)..(1)
<223> OTHER INFORMATION: Xaa on position 1 is any amino acid, preferably
      a negatively charged amino acid, more preferably Asp
<220> FEATURE:
<221> NAME/KEY: MISC_FEATURE
<222> LOCATION: (2)..(2)
<223> OTHER INFORMATION: Xaa on position 2 is a positively charged amino
      acid, preferably Arg
<220> FEATURE:
<221> NAME/KEY: MISC_FEATURE
<222> LOCATION: (3)..(3)
<223> OTHER INFORMATION: Xaa on position 3 is an aliphatic amino acid,
      such as Ile, Val, Leu, preferably Val
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (5)..(5)
<223> OTHER INFORMATION: Xaa on position 5 is an aliphatic amino acid,
      such as Ile, Leu, Val, preferably Ile
<220> FEATURE:
<221> NAME/KEY: MISC_FEATURE
<222> LOCATION: (8)..(8)
<223> OTHER INFORMATION: Xaa on position 8 is other than Pro, preferably
      Phe

<400> SEQUENCE: 7

Xaa Xaa Xaa Tyr Xaa His Pro Xaa
1               5


<210> SEQ ID NO 8
<211> LENGTH: 7
<212> TYPE: PRT
```

```
<213> ORGANISM: Artificial
<220> FEATURE:
<223> OTHER INFORMATION: Cyclic angiotensin peptide analog (Xaa 1-7)
<220> FEATURE:
<221> NAME/KEY: MISC_FEATURE
<222> LOCATION: (1)..(1)
<223> OTHER INFORMATION: Xaa on position 1 is any amino acid, preferably
      a negatively charged amino acid, more preferably Asp
<220> FEATURE:
<221> NAME/KEY: MISC_FEATURE
<222> LOCATION: (2)..(2)
<223> OTHER INFORMATION: Xaa on position 2 is a positively charged amino
      acid, preferably Arg
<220> FEATURE:
<221> NAME/KEY: MISC_FEATURE
<222> LOCATION: (3)..(3)
<223> OTHER INFORMATION: Xaa on position 3 is an aliphatic amino acid,
      such as Ile, Val, Leu, preferably Val
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (5)..(5)
<223> OTHER INFORMATION: Xaa on position 5 is an aliphatic amino acid,
      such as Ile, Leu, Val, preferably Ile

<400> SEQUENCE: 8

Xaa Xaa Xaa Tyr Xaa His Pro
1               5


<210> SEQ ID NO 9
<211> LENGTH: 7
<212> TYPE: PRT
<213> ORGANISM: Artificial
<220> FEATURE:
<223> OTHER INFORMATION: Cyclic angiotensin peptide analog (Xaa 2-8)
<220> FEATURE:
<221> NAME/KEY: MISC_FEATURE
<222> LOCATION: (1)..(1)
<223> OTHER INFORMATION: Xaa on position 1 is a positively charged amino
      acid, preferably Arg
<220> FEATURE:
<221> NAME/KEY: MISC_FEATURE
<222> LOCATION: (2)..(2)
<223> OTHER INFORMATION: Xaa on position 2 is an aliphatic amino acid,
      such as Ile, Val, Leu, preferably Val
<220> FEATURE:
<221> NAME/KEY: MISC_FEATURE
<222> LOCATION: (3)..(6)
<223> OTHER INFORMATION: Position 3-6 is a thioether-bridge
<220> FEATURE:
<221> NAME/KEY: MISC_FEATURE
<222> LOCATION: (4)..(4)
<223> OTHER INFORMATION: Xaa on position 4 is an aliphatic amino acid,
      such as Ile, Leu, Val, preferably Ile
<220> FEATURE:
<221> NAME/KEY: MISC_FEATURE
<222> LOCATION: (7)..(7)
<223> OTHER INFORMATION: Xaa on position 7 is other than Pro, preferably
      Phe

<400> SEQUENCE: 9

Xaa Xaa Tyr Xaa His Pro Xaa
1               5


<210> SEQ ID NO 10
<211> LENGTH: 6
<212> TYPE: PRT
<213> ORGANISM: Artificial
<220> FEATURE:
<223> OTHER INFORMATION: Cyclic angiotensin peptide analog (Xaa 3-8)
<220> FEATURE:
<221> NAME/KEY: MISC_FEATURE
```

```
<222> LOCATION: (1)..(1)
<223> OTHER INFORMATION: Xaa on position 1 is an aliphatic amino acid,
      such as Ile, Val, Leu, preferably Val
<220> FEATURE:
<221> NAME/KEY: MISC_FEATURE
<222> LOCATION: (2)..(5)
<223> OTHER INFORMATION: Position 2-5 is a thioether-bridge
<220> FEATURE:
<221> NAME/KEY: MISC_FEATURE
<222> LOCATION: (3)..(3)
<223> OTHER INFORMATION: Xaa on position 3 is an aliphatic amino acid,
      such as Ile, Leu, Val, preferably Ile
<220> FEATURE:
<221> NAME/KEY: MISC_FEATURE
<222> LOCATION: (6)..(6)
<223> OTHER INFORMATION: Xaa on position 6 is other than Pro, preferably
      Phe

<400> SEQUENCE: 10

Xaa Tyr Xaa His Pro Xaa
1               5


<210> SEQ ID NO 11
<211> LENGTH: 10
<212> TYPE: PRT
<213> ORGANISM: Artificial
<220> FEATURE:
<223> OTHER INFORMATION: General - Cyclic angiotensin peptide (Xaa1-10)
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 11

Asp Arg Val Tyr Ile His Pro Phe His Leu
1               5                   10


<210> SEQ ID NO 12
<211> LENGTH: 9
<212> TYPE: PRT
<213> ORGANISM: Artificial
<220> FEATURE:
<223> OTHER INFORMATION: General - Cyclic angiotensin peptide (Xaa1-9)
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 12

Asp Arg Val Tyr Ile His Pro Phe His
1               5


<210> SEQ ID NO 13
<211> LENGTH: 8
<212> TYPE: PRT
<213> ORGANISM: Artificial
<220> FEATURE:
<223> OTHER INFORMATION: General - Cyclic angiotensin peptide (Xaa1-8)
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 13

Asp Arg Val Tyr Ile His Pro Phe
1               5


<210> SEQ ID NO 14
<211> LENGTH: 7
<212> TYPE: PRT
<213> ORGANISM: Artificial
```

<220> FEATURE:
<223> OTHER INFORMATION: General - Cyclic angiotensin peptide (Xaa1-7)
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 14

Asp Arg Val Tyr Ile His Pro
1 5

<210> SEQ ID NO 15
<211> LENGTH: 7
<212> TYPE: PRT
<213> ORGANISM: Artificial
<220> FEATURE:
<223> OTHER INFORMATION: General - Cyclic angiotensin peptide (Xaa2-8)
<220> FEATURE:
<221> NAME/KEY: MISC_FEATURE
<222> LOCATION: (3)..(6)
<223> OTHER INFORMATION: Position 3-6 is a thioether-bridge

<400> SEQUENCE: 15

Arg Val Tyr Ile His Pro Phe
1 5

<210> SEQ ID NO 16
<211> LENGTH: 6
<212> TYPE: PRT
<213> ORGANISM: Artificial
<220> FEATURE:
<223> OTHER INFORMATION: General - Cyclic angiotensin peptide (Xaa3-8)
<220> FEATURE:
<221> NAME/KEY: MISC_FEATURE
<222> LOCATION: (2)..(5)
<223> OTHER INFORMATION: Position 2-5 is a thioether-bridge

<400> SEQUENCE: 16

Val Tyr Ile His Pro Phe
1 5

<210> SEQ ID NO 17
<211> LENGTH: 10
<212> TYPE: PRT
<213> ORGANISM: Artificial
<220> FEATURE:
<223> OTHER INFORMATION: Specific - Cyclic angiotensin peptide (Xaa1-10)
<220> FEATURE:
<221> NAME/KEY: MISC_FEATURE
<222> LOCATION: (4)..(4)
<223> OTHER INFORMATION: Xaa on position 4 is Abu or Ala
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (7)..(7)
<223> OTHER INFORMATION: Xaa on position 7 is Abu or Ala

<400> SEQUENCE: 17

Asp Arg Val Xaa Ile His Xaa Phe His Leu
1 5 10

<210> SEQ ID NO 18
<211> LENGTH: 9
<212> TYPE: PRT
<213> ORGANISM: Artificial
<220> FEATURE:
<223> OTHER INFORMATION: Specific - Cyclic angiotensin peptide (Xaa1-9)
<220> FEATURE:

```
<221> NAME/KEY: MISC_FEATURE
<222> LOCATION: (4)..(4)
<223> OTHER INFORMATION: Xaa on position 4 is Abu or Ala
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (7)..(7)
<223> OTHER INFORMATION: Xaa on position 7 is Abu or Ala

<400> SEQUENCE: 18

Asp Arg Val Xaa Ile His Xaa Phe His
1               5


<210> SEQ ID NO 19
<211> LENGTH: 8
<212> TYPE: PRT
<213> ORGANISM: Artificial
<220> FEATURE:
<223> OTHER INFORMATION: Specific - Cyclic angiotensin peptide (Xaa1-8)
<220> FEATURE:
<221> NAME/KEY: MISC_FEATURE
<222> LOCATION: (4)..(4)
<223> OTHER INFORMATION: Xaa on position 4 is Abu or Ala
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (7)..(7)
<223> OTHER INFORMATION: Xaa on position 7 is Abu or Ala

<400> SEQUENCE: 19

Asp Arg Val Xaa Ile His Xaa Phe
1               5


<210> SEQ ID NO 20
<211> LENGTH: 7
<212> TYPE: PRT
<213> ORGANISM: Artificial
<220> FEATURE:
<223> OTHER INFORMATION: Specific - Cyclic angiotensin peptide (Xaa1-7)
<220> FEATURE:
<221> NAME/KEY: MISC_FEATURE
<222> LOCATION: (4)..(4)
<223> OTHER INFORMATION: Xaa on position 4 is Abu or Ala
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (7)..(7)
<223> OTHER INFORMATION: Xaa on position 7 is Abu or Ala

<400> SEQUENCE: 20

Asp Arg Val Xaa Ile His Xaa
1               5


<210> SEQ ID NO 21
<211> LENGTH: 6
<212> TYPE: PRT
<213> ORGANISM: Artificial
<220> FEATURE:
<223> OTHER INFORMATION: Specific - Cyclic angiotensin peptide (Xaa2-7)
<220> FEATURE:
<221> NAME/KEY: MISC_FEATURE
<222> LOCATION: (3)..(3)
<223> OTHER INFORMATION: Can be Abu or Ala
<220> FEATURE:
```

<221> NAME/KEY: MISC_FEATURE
<222> LOCATION: (3)..(6)
<223> OTHER INFORMATION: position 3-6 is a thioether bridge
<220> FEATURE:
<221> NAME/KEY: MISC_FEATURE
<222> LOCATION: (6)..(6)
<223> OTHER INFORMATION: Can be Abu or Ala

<400> SEQUENCE: 21

Arg Val Xaa Ile His Xaa
1 5

<210> SEQ ID NO 22
<211> LENGTH: 8
<212> TYPE: PRT
<213> ORGANISM: Artificial
<220> FEATURE:
<223> OTHER INFORMATION: Specific 2 - Clyclic angiotensin peptide (Xaa1-8)
<220> FEATURE:
<221> NAME/KEY: MISC_FEATURE
<222> LOCATION: (4)..(4)
<223> OTHER INFORMATION: Xaa on position 4 is Abu
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 22

Asp Arg Val Xaa Ile His Ala Ile
1 5

<210> SEQ ID NO 23
<211> LENGTH: 8
<212> TYPE: PRT
<213> ORGANISM: Artificial
<220> FEATURE:
<223> OTHER INFORMATION: Specific 3 - Clyclic angiotensin peptide (Xaa1-8)
<220> FEATURE:
<221> NAME/KEY: MISC_FEATURE
<222> LOCATION: (4)..(7)
<223> OTHER INFORMATION: Position 4-7 is a thioether-bridge

<400> SEQUENCE: 23

Asp Arg Val Ala Ile His Ala Ile
1 5

<210> SEQ ID NO 24
<211> LENGTH: 29
<212> TYPE: PRT
<213> ORGANISM: Artificial
<220> FEATURE:
<223> OTHER INFORMATION: Angiotensin-containing fusion peptide
<220> FEATURE:
<221> NAME/KEY: MOD_RES
<222> LOCATION: (25)..(25)
<223> OTHER INFORMATION: may also be S
<220> FEATURE:
<221> NAME/KEY: MOD_RES
<222> LOCATION: (29)..(29)
<223> OTHER INFORMATION: F can be absent

<400> SEQUENCE: 24

Ile Thr Ser Ile Ser Leu Cys Thr Pro Gly Cys Lys Thr Gly Ala Leu
1 5 10 15

Met Ile Glu Gly Arg Asp Arg Val Thr Ile His Cys Phe
20 25

<210> SEQ ID NO 25

<211> LENGTH: 7
<212> TYPE: PRT
<213> ORGANISM: Artificial
<220> FEATURE:
<223> OTHER INFORMATION: Ang(1-7) analog
<220> FEATURE:
<221> NAME/KEY: MOD_RES
<222> LOCATION: (4)..(4)
<223> OTHER INFORMATION: Abu
<220> FEATURE:
<221> NAME/KEY: MISC_FEATURE
<222> LOCATION: (4)..(7)
<223> OTHER INFORMATION: thioether bridge

<400> SEQUENCE: 25

Asp Arg Val Xaa Ile His Ala
1 5

<210> SEQ ID NO 26
<211> LENGTH: 7
<212> TYPE: PRT
<213> ORGANISM: Artificial
<220> FEATURE:
<223> OTHER INFORMATION: Ang(1-7) analog
<220> FEATURE:
<221> NAME/KEY: MISC_FEATURE
<222> LOCATION: (4)..(4)
<223> OTHER INFORMATION: thioether bridge
<220> FEATURE:
<221> NAME/KEY: MOD_RES
<222> LOCATION: (7)..(7)
<223> OTHER INFORMATION: Abu

<400> SEQUENCE: 26

Asp Arg Trp Ala Ile His Xaa
1 5

<210> SEQ ID NO 27
<211> LENGTH: 7
<212> TYPE: PRT
<213> ORGANISM: Artificial
<220> FEATURE:
<223> OTHER INFORMATION: Ang(1-7) analog
<220> FEATURE:
<221> NAME/KEY: MISC_FEATURE
<222> LOCATION: (4)..(7)
<223> OTHER INFORMATION: thioether bridge

<400> SEQUENCE: 27

Asp Arg Val Ala Ile His Ala
1 5

<210> SEQ ID NO 28
<211> LENGTH: 8
<212> TYPE: PRT
<213> ORGANISM: Artificial
<220> FEATURE:
<223> OTHER INFORMATION: Ang(1-8) analog

<400> SEQUENCE: 28

Asp Arg Ile Thr Val His Cys Ile
1 5

<210> SEQ ID NO 29
<211> LENGTH: 8
<212> TYPE: PRT
<213> ORGANISM: Artificial
<220> FEATURE:
<223> OTHER INFORMATION: Ang(1-8) analog

<400> SEQUENCE: 29

-continued

```
Asp Arg Ile Thr Ile His Cys Ile
1               5


<210> SEQ ID NO 30
<211> LENGTH: 8
<212> TYPE: PRT
<213> ORGANISM: Artificial
<220> FEATURE:
<223> OTHER INFORMATION: Specific 2 - Clyclic angiotensin peptide
      (Xaa1-8)
<220> FEATURE:
<221> NAME/KEY: MISC_FEATURE
<222> LOCATION: (4)..(4)
<223> OTHER INFORMATION: Xaa on position 4 is Abu or Ala
<220> FEATURE:
<221> NAME/KEY: MISC_FEATURE
<222> LOCATION: (4)..(7)
<223> OTHER INFORMATION: Position 4-7 is a thioether-bridge
<220> FEATURE:
<221> NAME/KEY: MISC_FEATURE
<222> LOCATION: (7)..(7)
<223> OTHER INFORMATION: Xaa on position 7 is Abu or Ala

<400> SEQUENCE: 30

Asp Arg Val Xaa Ile His Xaa Ile
1               5
```

CYCLIC ANGIOTENSIN ANALOGS

Figure 1A:
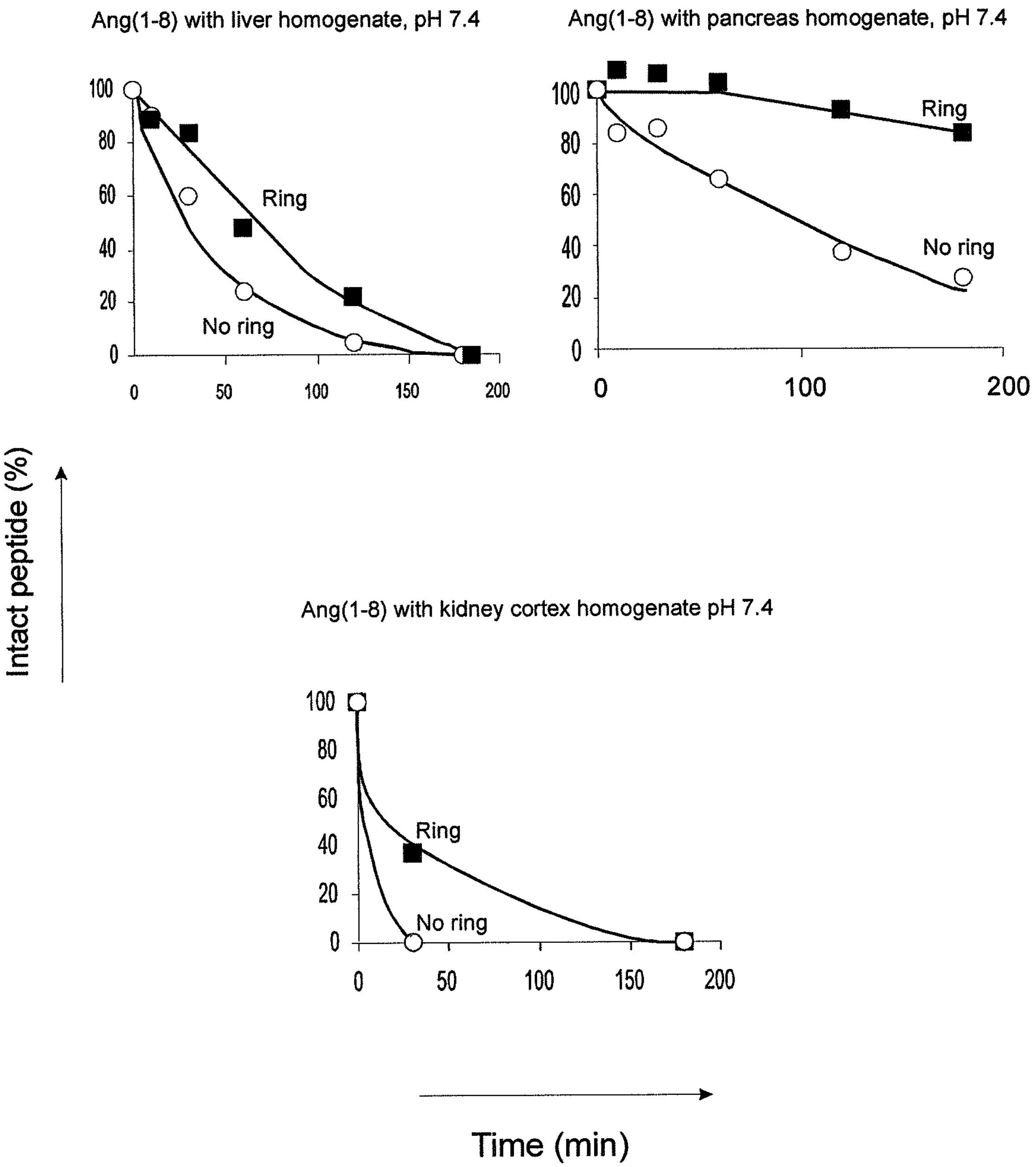

This application is the U.S. National Phase of, and Applicants claim priority from, International Application Number PCT/NL2007/050396 filed 7 Aug. 2007 and International Application Number PCT/NL2006/000414 filed 8 Aug. 2006 which are incorporated herein by reference.

BACKGROUND OF THE INVENTION

Incorporation of Sequence Listing

Incorporated herein by reference in its entirety is the Sequence Listing for the above-identified Application. The Sequence Listing is disclosed on a computer-readable ASCII text file titled "SequenceListing294-345PCTUS.txt", modified on Nov. 5, 2012. The sequence.txt file is 13.6 KB.

The invention relates to analogs of angiotensins, in particular to cyclised analogs having Ang(1-8) receptor agonistic and/or antagonistic activity, or Ang(1-7) receptor agonistic or antagonistic activity, and displaying improved proteolytic resistance compared to their linear counterparts. In particular, it relates to cyclised analogs having Ang(1-8) receptor antagonistic activity and Ang(1-7) receptor agonistic. Also provided is the therapeutic use of the cyclised peptide analogs.

The octapeptide angiotensin-II (Asp-Arg-Val-Tyr-Ile-His-Pro-Phe), also referred to as AngII or Ang(1-8) is one of the oldest peptide hormones, known for its multiplicity of biological actions related to endocrine or connected to the central and peripheral nervous system.

Ang(1-8) has multiple physiologic effects that regulate vascular tone, hormone secretion, tissue growth and neural activity. It has systemic and local effects, favoring cell growth and differentiation through four types of receptors. It may be applied in tissue repair and development. Antagonists of Ang (1-8) can be applied in antitumor action by inhibition of angiogenesis (Escobar et al 2004 Current Vascular Pharmacology 2, 385-399). Receptors of the renin angiotensin system (RAS) may be involved in the differentiation of stem cells (Ozturk et al 2004 Medical hypotheses 63, 866-874). Ang(1-8) receptor blockers are widely used for heart and renal failure and hypertension.

Ang(1-8) is a potent pressor agent, which has a vital role in the regulation of blood pressure, in the conservation of total blood volume and salt homeostasis. Furthermore, it is involved in the release of alcohol dehydrogenase (ADH), cell growth and the stimulation of the sympathetic system. Several antagonists of Ang(1-8) are efficient antipressor agents. Inadequate functioning of the renin-angiotensin system contributes substantially to the development of hypertension and cardiovascular and renal pathology (including left ventricular hypertrophy, structural alternations of the vasculature, neointima formation, nephrosclerosis, etc.).

Structure-activity relationships studies from several laboratories have revealed the topological contribution of the individual amino acid residues of the active Ang(1-8) molecule (Regoli et al., (1974) Pharmacol. Rev. 26, 69-123; Kholsa et al., (1974) Structure-activity relationship in angiotensin II analogs. In Handbook Exp. Pharmacol.—Angiotensin (Page, I. H. & Bumpus, F. M., eds), pp. 126-161. Springer-Verlag, Berlin; Cordopatis et al. (1999) In Bioactive Peptides in Drug Discovery and Design. Medical Aspects (Matsoukas, J. & Mavromoustakos, T., eds), pp. 25-32. IOS Press, Amsterdam, NL). These studies have included theoretical, physicochemical, and spectroscopic investigation and have led to several models for the Ang(1-8) structure in solution.

Ang(1-8) is produced by the conversion of its precursor decapeptide angiotensin-I (Asp-Arg-Val-Tyr-Ile-His-Pro-Phe-His-Leu; herein also referred to as AngI or Ang(1-10)) to Ang(1-8) by the action of the angiotensin-I converting enzyme (ACE) of the vascular endothelium. Upon ACE hydrolysis, the inactive Ang(1-10) is converted to the biologically active Ang(1-8). The two peptides differ in the length and nature of their C-terminus; Ang(1-8) lacks the His-Leu terminal dipeptide. Ang(1-10) is generated in the circulation by the action of renin from the kidneys on its substrate, called alpha2-globulin or angiotensinogen, produced in the liver (Do et al., J. Biol. Chem. 262, 1037-1043).

ACE is a target for inactivation by ACE inhibitor drugs, which decrease the rate of angiotensin II production. The renin-angiotensin system plays a critical role in blood pressure control and body fluid and electrolyte homeostasis. Besides Ang(1-8), several other cleavage products of Ang(1-10) have been identified, for example, Ang(1-9), Ang(1-7), Ang III (Ang(2-8)), and Ang IV (Ang(3-8)).

Angiotensin-(1-7) (Ang(1-7)), a heptapeptide biologically active member of the renin-angiotensin peptide family, antagonizes the RAS system at various levels. Being a substrate for ACE, Ang(1-7) competes with Ang I and bradykinin for degradation, thereby inhibiting Ang II formation and augmenting bradykinin activity. Ang(1-7) has also been found to block the deleterious actions of Ang II through a noncompetitive blockade of AT1 receptors and direct stimulation of angiotensin type 2 (AT2) receptors. Although ACE inhibitors were originally developed to suppress the formation of Ang II, part of their beneficial effect in cardiovascular diseases may be attributed to the resultant elevation in Ang(1-7) levels. ACE inhibitor treatment, although having limited effects on the circulating amount of Ang II, increases Ang(1-7) levels 10- to 25-fold.

Intravenous infusion of Ang(1-7) inhibited smooth muscle cell proliferation associated with balloon-catheter injury (Strawn W. B. et al. Angiotensin(1-7) reduces smooth muscle growth after vascular injury, Hypertension 33:207-11, 1999). Ang(1-7) also opposes the mitogenic response to Ang II in cultured VSMCs. Further, Ang(1-7), through interaction with its recently discovered Ang(1-7) receptor, has a vasodilatory effect by way of stimulating nitric oxide release.

Ang(1-7) has become an angiotensin of particular interest in the past few years, because its cardiovascular and baroreflex actions counteract those of Ang(1-8). Unique angiotensin-binding sites specific for this heptapeptide and studies with a selective Ang(1-7) antagonist indicated the existence of a distinct Ang(1-7) receptor. Santos R A, et al. (Proc Natl Acad Sci USA. 2003 Jun. 26) demonstrated that genetic deletion of the G protein-coupled receptor encoded by the Mas protooncogene abolishes the binding of Ang(1-7) to mouse kidneys. Accordingly, Mas-deficient mice completely lack the antidiuretic action of Ang(1-7) after an acute water load. Ang(1-7) binds to Mas-transfected cells and elicits arachidonic acid release. Furthermore, Mas-deficient aortas lose their Ang(1-7)-induced relaxation response. Collectively, these findings identify Mas as a functional receptor for Ang (1-7) and provide a clear molecular basis for the physiological actions of this biologically active peptide.

Both Ang(1-8) and Ang(1-7) have been shown to facilitate tissue repair like in skin wound healing (Yahata et al (2006) J Biol. Chem 281, 13209-13216) and after artery stent placement (Langeveld et al (2005) Hypertension 45, 138-141). Also, beneficial effect on bone marrow suppression during chemotherapy has been shown. In contrast to Ang(1-8), Ang (1-7) does not possess the adverse hypertensive properties. This makes especially Ang(1-7), and analogs thereof, of interest for these applications.

Ang(1-7) and Ang(1-8) have been reported to play a role in multiple other therapeutic effects. Ang(1-7) may have a beneficial role before and after chemotherapy in patients with newly diagnosed breast cancer (Rodgers et al 2006 Cancer Chemother Pharmacol 57, 559-568) and it inhibits lung cancer, in vitro, (Gallagher & Tallant. 2004. Carcinogenesis 25, 2045-2052). Ang(1-7) inhibits growth of human adenocarcinoma xenografts in nude mice through a reduction in cyclooxygenase-2 (Menon, Soto-Pantaja, Callahan, Clin, Ferrario, Tallant & Gallagher 2007 Cancer Res. 67:2809-15.) Angiotensin(1-7) prevents diabetes-induced cardiovascular dysfunction (Benter, Yousif, Cojocel, Al-Maghrebi, Diz 2007 Am J Heart Circ Physiol 292, H666-72.)

Ang(1-8) is degraded in the body to angiotensin III (Arg-Val-Tyr-Ile-His-Pro-Phe; or Ang(2-8) by angiotensinases that are located in red blood cells and the vascular beds of most tissues. It has a half-life in humans of 1-2 minutes. Angiotensin III has 40% of the pressor activity of Angiotensin II, but 100% of the aldosterone-producing activity.

Angiotensin IV (Val-Tyr-Ile-His-Pro-Phe; or Ang(3-8) is a hexapeptide which, like angiotensin III, has some lesser activity.

Angiotensins II, III & IV have a number of effects throughout the body. For example, they have, cardiovascular effects because they are potent and direct vasoconstrictors, constricting arteries and veins and increasing blood pressure. Angiotensin II has prothrombotic potential through adhesion and aggregation of platelets and production of PAI-1 and PAI-2. It has been thought that angiotensin II could be a cause of vascular and cardiac muscle hypertrophy.

Furthermore, Ang(1-8) increases thirst sensation through the subfornical organ (SFO) of the brain, decreases the response of the baroreceptor reflex, and increases the desire for salt. It increases the secretion of ADH in the posterior pituitary and ACTH in the anterior pituitary. It also potentiates the release of norepinephrine by direct action on postganglionic sympathetic fibers.

Ang(1-8) acts also on the adrenal cortex, causing it to release aldosterone, a hormone that causes the kidneys to retain sodium and lose potassium. Elevated plasma angiotensin II levels are responsible for elevated aldosterone levels during the luteal phase of the menstrual cycle.

Ang(1-8) also has trophic effects on the vasculature, promoting growth of the muscles in the arterial wall. It is also thought to be angiogenic, i.e. it causes vascularisation of newly developing tissue.

In addition, Ang(1-8) has a direct effect on the proximal tubules to increase $Na^+$ resorption. Although it slightly inhibits glomerular filtration by indirectly (through sympathetic effects) and directly stimulating mesangial cell constriction, its overall effect is to increase the glomerular filtration rate by increasing the renal perfusion pressure via efferent renal constriction.

Clearly, the family of angiotensin hormone peptides is involved in mediating important physiological effects. Accordingly, the development of angiotensin analogs, having either agonist or antagonist activity, that are of use as therapeutic agents has received a lot of attention. However, the medical and industrial application of small, linear peptides is severely restricted by their limited stability. It is well known in the art of peptide drug design that cyclization of a linear peptides can induce structural rigidity, thereby preventing degradation. Furthermore, if designed carefully without causing drastic changes in the conformation of active peptides, the rigid geometry of the cyclic peptides may enhance the binding affinity towards a selected target molecule compared to their linear counterparts. Also, cyclic analogs can serve as important intermediates in the design and synthesis of non-peptide mimetics with the potential to be used as drugs.

During the last decades, numerous cyclization methods have been applied for the preparation of mono- and bicyclic peptides. In many cases, the objective was to probe the bioactive conformation(s) of a target peptide by reducing the conformational stability or to produce more metabolically stable compounds. Disulfide and amide cyclizations are among the most commonly used monocyclization methods (Hruby et al., Biochem J. 1990 Jun. 1; 268(2):249-62), but other strategies have also been employed including, for example, thioether-cyclizations (Feng et al., Organic Lett. 1999, 1, 121; Jones et al., Tetrahedron Lett. 1998, 39, 6107; WO93/03056).

A number of different conformationally restricted cyclized Ang(1-8) analogs have been described in the art. Cyclization was achieved among others by the disulfide method using cysteine moieties at various positions of the peptide molecule or by the amide-linkage method. See for example Miura et al., J Biol Chem. 1999 Mar. 12; 274(11):7103-10; Miranda et al., Braz J Med Biol Res. 1988; 21(5):903-14; Spear et al., J Med Chem. July 1990; 33(7):1935-40; Nikiforovich et al., Biochemistry. 1994 Mar. 29; 33(12):3591-8; Zhang et al., J Med Chem. 1996 Jul. 5; 39(14):2738-44). Poleyava et al. (Bioorg Med Chem. June 2001; 9(6):1639-47) disclosed a constrained cyclic AngII analog with a lactam amide bridge linking a Lys-Glu pair at positions 3 and 5 of the peptide and possessing Ile at position 8. This analog was found to be an inhibitor of AngII. Lindmann et al., (Bioorg Med Chem. March 2001; 9(3):763-72) described cyclic 12-, 13- and 14-atom membered ring AngII analogs encompassing methylene-dithioether bridges.

Other structure-activity studies have illustrated the importance of the C-terminal residue Phe for agonistic activity of Ang(1-8). Replacement of $Phe^8$ with an aliphatic one, e.g. Ile, results in an antagonist [Sar1-Ile8] AngII, also known as Sarilesin (Mavromoustakos et al., J. Med. Chem., 1999, 42, 1714; Ganter et al., J. Med. Chem. 1995, 38, 4660). Mutation studies have also shown that the aromaticity of $Phe^8$ position is important for receptor activation (Roumelioti et al., Bioorg. Med. Chem. Lett. 2000, 10, 1).

The above illustrates that there is a great interest in the development of novel angiotensin analogs. The present inventors set out to design and synthesize further angiotensin analogs which display biological activity and which are metabolically stable. In particular, they aimed to provide Ang(1-8) and Ang(1-7) analogs which display enhanced resistance to proteolytic degradation as compared to their linear counterparts while retaining a biological activity, said biological activity being either of the same type or of a different type. A further aim was to converting an Ang agonist into an Ang antagonist, or vice versa.

These goals are met by the surprising finding that the introduction of a thioether-ring structure between the amino acids corresponding to positions 4 and 7 in naturally occurring angiotensins (e.g. Ang(1-8) or Ang(1-10), $Tyr^4$ and $Pro^7$, results in a biologically active angiotensin-analog having an enhanced resistance against proteases.

The increased proteolytic resistance of the therapeutic Ang-analog, or a precursor thereof, allows for a much higher therapeutic potential, lower dose and/or a lower frequency of administration, and may allow effective oral administration. Furthermore, an overall increase in stability may allow for an increased shelf-life of the peptide analog.

DESCRIPTION OF THE INVENTION

Accordingly, the invention provides a cyclic angiotensin peptide analog comprising a thioether-bridge linkage between the amino acids corresponding to positions $Tyr^4$ and $Pro^7$ in linear, naturally occurring angiotensin, like in human AngI (Ang(1-10).

Biologically active angiotensin analogs wherein the amino acids at positions 4 and 7 (all positions referred to herein correspond to the numbering as in naturally occurring Ang, unless indicated otherwise) are modified to a cyclic structure have not been previously disclosed. In fact, it is highly surprising that modification of $Tyr^4$ does not abolish the biological activity of an angiotensin for the following reasons. Accumulated experimental evidence for AngII supports a bioactive conformation characterized by a charge relay system between Tyr hydroxyl, His imidazole and Phe carboxylate, analogous to that found in serine proteases, as well as a ring cluster of the triad key amino acids $Tyr^4$-$His^6$-$Phe^8$ which is suggested to be responsible for activity. The ring cluster conformation was supported by the design and synthesis of a novel constrained AngII cyclic analog, [Sar1-Lys3-Glu5] AngII (Matsoukas et al. Bioorg. Med. Chem. 2000, 8, 1).

Furthermore, interactions between $Tyr^4$ and $Phe^8$ of Ang (1-8) with $Asn^{111}$ and $His^{256}$, respectively, of the AngII type I (AT1) receptor were reported to be essential for agonistic activity (Noda et al., (1996) Biochemistry, 35, 16435). Miura et al. (1999, J. Biol. Chem., Vol. 274, No. 11, pp. 7103) subsequently reported that it is primarily the aromaticity, and secondarily the size of the $Tyr^4$ side chain that is important in activating the receptor. Beta-cyclohexylalanine replacements at either position 4 or 8 hindered ligand-dependent activation of the receptor.

In view of the above evidence for $Tyr^4$ being critical for angiotensin function, the present finding that a thioether-ring structure can be introduced at positions 4 and 7 without compromising biological activity is clearly unexpected. The expression "without compromising biological activity" is meant to indicate that the cyclised analog has at least some activity in vitro and/or in vivo. In qualitative terms, the nature of the activity can be identical to that of the linear counterpart, e.g. a linear Ang(1-7) peptide having agonistic activity is cyclised to yield a more stable agonist, or the activity can be different, e.g. a linear agonist becoming an antagonist when cyclised through the residues at positions 4 and 7. In quantitative terms, it is noted that for a cyclic analog the activity need not be as high as the linear counterpart; a loss of 90% of activity upon ring introduction can still yield a peptide of great interest if its stability is 1000 times higher than its linear counterpart.

A thioether bridge is also referred to as a monosulfide bridge or, in the case of Ala-S-Ala, as a lanthionine bridge. Thioether-bridge containing peptides can be formed by two amino acids having either one of the following general formulas:

Formula A

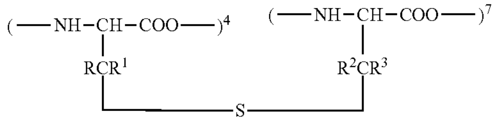

-continued

Formula B

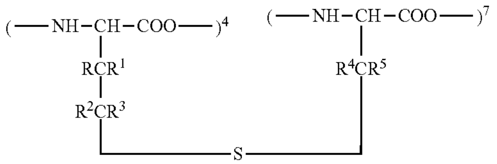

Formula C

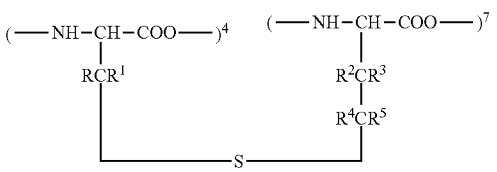

wherein $R^1$, $R^2$, $R^3$, $R^4$ and $R^5$ are independently selected from —H, a lower (e.g. $C_1$-$C_{10}$) alkyl or aralkyl group. In a preferred embodiment, $R^1$, $R^2$, $R^3$, $R^4$ and $R^5$ are independently selected from H and $CH_3$.

In one embodiment, the invention provides a peptide comprising a thio-ether bridge according to formula A, i.e. wherein the linkage between the amino acids at positions 4 and 7 has the meaning —$RCR^1$—S—$R^2CR^3$—, wherein R, $R^1$, $R^2$ and $R^3$ are independently selected from —H, a lower (e.g. $C_1$-$C_{10}$ alkyl or aralkyl group. R, $R^1$, $R^2$ and $R^3$ are preferably independently selected from H and $CH_3$. Peptides comprising a thio-ether bridge according to formula A can be made for example by lantibiotic enzymes or by sulfur extrusion from a disulfide. The disulfide from which the sulfur is extruded can be formed by a D-cysteine in position 4 and a L-cysteine in position 7 or by one D-cysteine in position 4 and a L-penicillamine in position 7 [Galande, Trent and Spatola 2003 Biopolymers 71, 534-551].

Alternatively, the linkage of the two amino acids can be composed of $RCR^1$—$R^2CR^3$—S—$R^4CR^5$ (Formula B) or $RCR^1$—S—$R^4CR^5$—$R^2CR^3$ (Formula C), in which R, $R^1$, $R^2$, $R^3$, $R^4$ and $R^5$ independently represent —H, a lower (e.g. $C_1$-$C_{10}$) alkyl or aralkyl group. Peptides comprising a thio-ether bridge according to formula B can for instance be made by sulfur extrusion of a disulfide formed by a D-homocysteine in position 4 and a L-cysteine in position 7 [Galande, Trent and Spatola 2003 Biopolymers 71, 534-551]. Likewise, peptides comprising a thio-ether bridge according to formula C can for instance be made by sulfur extrusion of a disulfide formed by a D-cysteine in position 4 and a L-homocysteine in position 7 [Galande, Trent and Spatola 2003 Biopolymers 71, 534-551].

It is convenient that a peptide analog of the invention can be made in a biological system, in particular making use of the lantibiotic enzyme system of a (bacterial) host cell. Accordingly, peptides comprising a thioether-bridge according to formula A are preferred.

The term "cyclic angiotensin peptide analog" refers to any angiotensin analog having biological activity and/or being capable of selective receptor binding, or an inactive precursor thereof which can be proteolytically activated, e.g. in a fashion that is similar to Ang(1-10) conversion to active fragments. The analog will typically not contain an amino acid sequence that is unrelated to angiotensin function and/or processing, such as a lantibiotic leader peptide sequence. The size of a peptide analog can vary but ranges between 4 to 10 amino acids, as long as the "core" tetrameric segment comprising the 4-7 thioether-ring structure is encompassed. Preferred analogs contain 4-8 amino acids, more preferably 5-8 amino acids. In a specific aspect, the analog consists of 7 amino acid residues, preferably corresponding to those of naturally occurring Ang(1-7).

The amino acid sequence of an analog of the invention can vary, as long as it is biologically active, either agonistically or antagonistically or can become proteolytically activated. Biological activity of an analog can be determined using methods known in the art, including radioligand binding studies, in vitro cell activation assays and in vivo experiments. See for example Koziarz et al., 1993 Gen. Pharmacol. 24, 705-713; Lemos et al 2005 J Cardiovasc Pharmacol 46, 274-279; Santos et al 2003 PNAS 100: 8258-8263; Godeny and Sayeski 2006 Am J Physiol Cell Physiol.; 291(6):C1297-307; Sarr et al., Cardiovasc Res. 2006 Sep. 1; 71(4):794-802; Silva et al 2007 Peptides 28, 702-707.

In one embodiment the invention provides a 4,7-cyclised analog designated $[Cyc^{4-7}]$Ang(1-10) derived from natural Angiotensin I (Ang(1-10).

In another embodiment the invention provides a 4,7-cyclised analog designated $[Cyc^{4-7}]$Ang(1-8) derived from natural Angiotensin II (Ang(1-8).

In another embodiment the invention provides a 4,7-cyclised analog designated $[Cyc^{4-7}]$Ang(2-8) derived from natural Angiotensin III (Ang(2-8).

In another embodiment the invention provides a 4,7-cyclised analog designated $[Cyc^{4-7}]$Ang(3-8) derived from natural Angiotensin IV (Ang(3-8).

In another embodiment the invention provides a 4,7-cyclised analog designated $[Cyc^{4-7}]$Ang(1-7) derived from natural Ang(1-7).

In another embodiment the invention provides a 4,7-cyclised analog designated $[Cyc^{4-7}]$Ang(1-9) derived from natural Ang(1-9).

The expression "derived from" is meant to indicate that the peptide sequence essentially corresponds to that of the naturally occurring linear Ang peptide. As compared to the amino acid sequence of the natural angiotensin peptide, the amino acids at positions 4 and 7 of the $[Cyc^{4-7}]$ analog are modified to allow introduction of the thioether-ring structure (see above). As will be understood, the amino acids at the other positions can be the same or they can be different, provided that the analog is biologically active. Preferably, besides the residues 4 and 7, zero, one or two residues are different from those found in the corresponding natural sequence, more preferably zero or one.

The function of the cyclic analog can be the same (e.g. agonist remains agonist) as or opposite to (e.g. agonist becomes antagonist) that of its linear counterpart. In case of analogs of inactive precursors, like $[Cyc^{4-7}]$Ang(1-10), biological function means both its susceptibility to (ACE-)enzymes that can convert it to a biologically active fragment (e.g. Ang(1-8) or Ang(1-7)) as well as the biological activity of the fragment itself.

Structure-activity relationships studies from several investigators have revealed the contribution of the individual amino acid residues to the activity of natural angiotensins (see Spyroulias et al. Eur. J. Biochem. 270, 2163, and references cited therein). These results can be used to predict to what extent a given amino acid can be altered in an analog of the present invention without loosing biological activity.

For example, it was found that the amino acid at position 1 in Ang(1-8) is not crucial for its activity, but that it is preferably a negatively charged amino acid, more preferably Asp.

The amino acid at position 2 is preferably a positively charged amino, preferably Arg.

The amino acid at position 3 is preferably an aliphatic residue, for example Ile or Val, preferably Val.

The amino acid at position 5 is preferably an aliphatic residue, for example Ile or Val, preferably Ile.

The amino acid at position 6 is preferably His, based on the finding that progressive destruction of the $His^6$ imidazole UV irradiation diminished Ang(1-8) activity (Samanen et al., J. Med. Chem. 31, 737-741).

The amino acid at position 8 in $[Cyc^{4-7}]$Ang(1-9) or at position 9 in $[Cyc^{4-7}]$Ang(1-10) is preferably other than Pro to allow for proteolytic activation.

Poleyava et al. (Bioorg Med Chem. June 2001; 9(6):1639-47) disclosed that a constrained cyclic Ang(1-8) analog with a lactam amide bridge linking a Lys-Glu pair at positions 3 and 5 and possessing Ile at position 8 is an inhibitor of Ang (1-8). Thus, a $[Cyc^{4-7}]$analog of the invention can be designed having an aliphatic residue at position 8, preferably Ile, to confer an inhibitory effect on Ang(1-8) e.g. the analog $[Cyc^{4-7}]$Ang(1-8)F8I. To maintain the biological activity of Ang(1-10), a Phe residue at position 8 is preferred.

For each of the analogs, the preferred amino acid at position 9 is His.

For each of the analogs, the preferred amino acid at position 10 is an aliphatic residue, for example Ile, Val or Leu, of which Leu is preferred.

As will be understood, an analog may contain the above preferred residues for each amino acid position in any combination.

Accordingly, the invention provides a cyclic angiotensin peptide analog comprising a thioether-bridge linkage between the amino acids corresponding to positions $Tyr^4$ and $Pro^7$ in the linear octapeptide Angiotensin II (Ang(1-8)), said analog having the general formula $[Cyc^{4-7}]$ $Xaa^{1-10}$, $[Cyc^{4-7}]$ $Xaa^{1-9}$, $[Cyc^{4-7}]$ $Xaa^{1-8}$, $[Cyc^{4-7}]$ $Xaa^{1-7}$, $[Cyc^{4-7}]$ $Xaa^{2-8}$ or $[Cyc^{4-7}]$ $Xaa^{3-8}$, wherein, if applicable, $Xaa^1$ is any amino acid, preferably a negatively charged amino acid, more preferably Asp;

$Xaa^2$ is a positively charged amino acid, preferably Arg;

$Xaa^3$ is an aliphatic amino acid, such as Ile, Val, preferably Val;

$Xaa^5$ is an aliphatic amino acid, such as Ile, Val, preferably Ile;

$Xaa^6$ is His;

$Xaa^8$ is other than Pro, preferably Phe;

$Xaa^9$ is other than Pro, preferably His;

$Xaa^{10}$ is an aliphatic amino acid, such as Ile, Leu, Val, preferably Leu.

The general formula $[Cyc^{4-7}]$ $Xaa^{1-10}$ refers to a peptide consisting of amino acids $Xaa^1$-$Xaa^2$-$Xaa^3$-$Xaa^4$-$Xaa^5$-$Xaa^6$-$Xaa^7$-$Xaa^8$-$Xaa^9$-$Xaa^{10}$, wherein the peptide is cyclized via $Xaa^4$ and $Xaa^7$. Likewise, the general formula $[Cyc^{4-7}]$ $Xaa^{1-7}$ refers to a peptide consisting of amino acids $Xaa^1$-$Xaa^2$-$Xaa^3$-$Xaa^4$-$Xaa^5$-$Xaa^6$-$Xaa^7$, wherein the peptide is cyclized via $Xaa^4$ and $Xaa^7$. Likewise, the general formula $[Cyc^{4-7}]$ $Xaa^{2-8}$ refers to a peptide consisting of amino acids $Xaa^2$-$Xaa^3$-$Xaa^4$-$Xaa^5$-$Xaa^6$-$Xaa^7$-$Xaa^8$, wherein the peptide is cyclized via $Xaa^4$ and $Xaa^7$.

In one embodiment, the peptide analog has the general formula $[Cyc^{4-7}]$ $Xaa^{1-10}$, $[Cyc^{4-7}]$ $Xaa^{1-9}$, $[Cyc^{4-7}]$ $[Cyc^{4-7}]$ $Xaa^{1-8}$, $[Cyc^{4-7}]$ $Xaa^{1-7}$, $[Cyc^{4-7}]$ $Xaa^{2-7}$, $[Cyc^{4-7}]$ $Xaa^{3-7}$, $[Cyc^{4-7}]$ $Xaa^{2-8}$ or $[Cyc^{4-7}]$ $Xaa^{3-8}$, wherein all but three, preferably all but two, more preferably all but one of the residues other than $Xaa^4$ and $Xaa^7$ are identical to those found in naturally occurring Ang(1-10), i.e. wherein $Xaa^1$ is Asp, $Xaa^2$ is Arg, $Xaa^3$ is Val, $Xaa^5$ is Ile, $Xaa^6$ is His, $Xaa^8$ is Phe, $Xaa^9$ is His, $Xaa^{10}$ is Leu. In a specific aspect, the peptide analog has the general formula $[Cyc^{4-7}]$ $Xaa^{1-10}$, $[Cyc^{4-7}]$ $Xaa^{1-9}$, $[Cyc^{4-7}]$ $[Cyc^{4-7}]$ $Xaa^{1-8}$, $[Cyc^{4-7}]$ $Xaa^{1-7}$, $[Cyc^{4-7}]$ $Xaa^{2-7}$, $[Cyc^{4-7}]$ $Xaa^{3-7}$, $[Cyc^{4-7}]$ $Xaa^{2-8}$ or $[Cyc^{4-8}]$ $Xaa^{3-8}$, wherein $Xaa^1$ is Asp, $Xaa^2$ is Arg, $Xaa^3$ is Val, $Xaa^5$ is Ile, $Xaa^6$ is His, $Xaa^8$ is Phe, $Xaa^9$ is His, $Xaa^{10}$ is Leu.

In a preferred embodiment, the peptide has the general formula $[Cyc^{4-7}]$ $Xaa^{1-7}$. As is shown herein below, this Ang (1-7) analog has Ang(1-8) antagonistic and Ang(1-7) agonistic activity, combined with an increased proteolytic resistance when compared to unmodified, linear Ang(1-7). Thus far, no conformationally constraint analogs of Ang(1-7) have been described. The present finding that it is possible to modify two out of seven amino acids (i.e. a change in nearly 30% of the side chains) without losing biological activity is unexpected. What is more, the increased resistance towards proteolytic enzymes upon introduction of the 4,7-thioether ring could not be anticipated.

In a peptide analog according to the general formula $[Cyc^{4-7}]$ $Xaa^{10}$, $[Cyc^{4-7}]$ $Xaa^{1-9}$, $[Cyc^{4-7}]$ $[Cyc^{4-7}]$ $Xaa^{1-8}$, $[Cyc^{4-7}]$ $Xaa^{1-7}$, $[Cyc^{4-7}]$ $Xaa^{2-7}$, $[Cyc^{4-7}]$ $Xaa^{3-7}$, $[Cyc^{4-7}]$ $Xaa^{2-8}$ or $[Cyc^{4-7}]$ $Xaa^{3-8}$, the residues $Xaa^4$ and $Xaa^7$ together form a thioether-bridge. Preferably, $Xaa^4$ is a D-stereoisomer and/or $Xaa^7$ is a L-stereoisomer. More preferably, $Xaa^4$ is a D-stereoisomer and $Xaa^7$ is a L-stereoisomer. The thioether bridge is for instance in accordance with formula A, B or C as indicated above. Formula A is preferred.

In one embodiment, the amino acids at positions 4 and 7 are independently selected from Abu (2-aminobutyric acid) and Ala (alanine), with the exception of Abu being present at both positions 4 and 7. Thus, encompassed are cyclic analogs comprising a thioether linkage formed by $-Ala^4$-S-$Ala^7$-(Formula A: R, $R^1$, $R^2$ and $R^3$ being H); $-Ala^4$-S-$Abu^7$-(Formula A: R, $R^1$ being H, one of $R^2$ and $R^3$ being H and the other being $CH_3$) or $-Abu^4$-S-$Ala^7$-(Formula A: one of R and $R^1$ being H the other being $CH_3$, $R^2$ and $R^3$ being H). Specific cyclic analogs comprise a $-Abu^4$-S-$Ala^7$- or $Ala^4$-S-$Ala^7$-linkage (see also FIG. 7).

In a specific aspect, the angiotensin analog is selected from the group consisting of the following 4,7-thioether cyclised peptides:

```
the [Cyc4-7]Ang(1-10) analog
Asp-Arg-Val-Abu/Ala-Ile-His-Abu/Ala-Phe-His-Leu

the [Cyc4-7]Ang(1-9) analog
Asp-Arg-Val-Abu/Ala-Ile-His-Abu/Ala-Phe-His

the [Cyc4-7]Ang(1-8) analog
Asp-Arg-Val-Abu/Ala-Ile-His-Abu/Ala-Phe

the [Cyc4-7]Ang(1-8) analog
Asp-Arg-Val-Abu/Ala-Ile-His-Abu/Ala-Ile

the [Cyc4-7]Ang(1-7) analog
Asp-Arg-Val-Abu/Ala-Ile-His-Abu/Ala

the [Cyc4-7]Ang(2-7) analog
Arg-Val-Abu/Ala-Ile-His-Abu/Ala
```

under the provision that Abu is not present simultaneously at positions 4 and 7. In other words, the peptide does not contain two Abu (2-aminobutyric acid) residues.

In a preferred aspect, the analog is selected from the group consisting of

```
the [Cyc4-7]Ang(1-10) analog
Asp-Arg-Val-Abu/Ala-Ile-His-Abu/Ala-Phe-His-Leu,

the [Cyc4-7]Ang(1-9) analog
Asp-Arg-Val-Abu/Ala-Ile-His-Abu/Ala-Phe-His
```

-continued

```
the [Cyc4-7]Ang(1-8) analog
Asp-Arg-Val-Abu/Ala-Ile-His-Abu/Ala-Ile,

the [Cyc4-7]Ang(1-7) analog
Asp-Arg-Val-Abu/Ala-Ile-His-Abu/Ala
and

the [Cyc4-7]Ang(2-7) analog
Arg-Val-Abu/Ala-Ile-His-Abu/Ala.
```

In particular, provided is an Ang(1-7) analog with a thioether-bridge between position 4 and position 7 having the amino acid sequence Asp-Arg-Val-Abu-Ile-His-Ala, Asp-Arg-Val-Ala-Ile-His-Abu or the amino acid sequence Asp-Arg-Val-Ala-Ile-His-Ala. These analogs antagonize constriction in the trachea smooth muscle by natural angiotensin(1-8). This activity appeared comparable to that of the natural linear Ang(1-7) peptide, DRVYIHP. It was surprisingly found that these analogs also cause vasodilation of phenylephrine-induced vasoconstriction in aorta from Sprague Dawley rats, indicating that the ring introduction preserves Ang(1-7) receptor agonistic activity.

Modification of the Pro residue at position 7 of linear Ang(1-7) has been described in the art. Santos et al. (Proc Natl Acad Sci USA 2003; 100:8258-63), demonstrated that Ang (1-7) peptide wherein the original Pro residue at position 7 is replaced by D-Ala is converted into an Ang(1-7) receptor antagonist. Another study (Da Silva et al. Peptides 28 (2007), 702-707) likewise shows that a mutant, linear Ang(1-7) peptide wherein the original L-Pro at position 7 is replaced by D-Pro acts in Sprague Dawley rats, as an Ang(1-7) receptor antagonist, likely of a different Ang(1-7) receptor than in the above study of Santos et al which involves Chinese Hamster Ovary cells. In view of these published data, the present finding that Ang(1-7) agonist activity is preserved upon introduction of a substantive modification at position 7 in 4,7-cyclic Ang(1-7) is therefore highly surprising.

In a still further embodiment, an angiotensin(1-8) analog is provided having Ang(1-8) receptor antagonistic activity and having the sequence Asp-Arg-Val-Abu-Ile-His-Ala-Ile.

Also provided is a pharmaceutical composition comprising a 4,7-cyclised angiotensin analog of the invention, or a pharmaceutically acceptable salt or complexes thereof, and a pharmaceutically acceptable carrier As used herein, "acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminium, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

In one aspect, the invention provides a method for the treatment or prophylaxis of a disease involving unwanted vasoconstriction, comprising administering to a subject in need thereof a therapeutically effective dose of an angiotensin analog according to the present teachings having Ang(1-8) antagonistic activity, or a pharmaceutically acceptable salt or complexes thereof. The subject is preferably a human subject, for example a human hypertensive or asthmatic subject.

Preferably, the composition comprises a cyclized analog having Ang(1-8) receptor antagonistic and/or Ang(1-7) receptor agonistic activity. Thus, an analog may have Ang(1-8) antagonistic activity e.g. by blocking the Ang(1-8) receptor and/or it may have Ang(1-7) agonistic activity, e.g. by binding to an Ang(1-7) receptor, in particular the Mas-receptor, in combination with subsequent signal transmission. Ang(1-8) antagonistic activity does not necessarily imply Ang(1-7) agonistic activity, and vice versa.

The person skilled in the art will be able to determine whether an analog of the invention possesses Ang(1-8) antagonistic or agonistic activity using methods known in the art. As shown herein below, trachea rings of guinea pigs can be used to determine the capacity of an analog to induce contraction of the trachea smooth muscle (indicative of agonistic activity) or the capacity of an analog to inhibit contraction of the trachea smooth muscle induced by "normal" Ang (1-8), which is indicative of antagonistic activity. Also it is shown that aorta rings of Sprague-Dawley rats can be used to determine the capacity of an Ang(1-7) analog to induce dilatation of phenylephrine-induced contraction. Other types of assays, for instance in vitro cell activation assays, can also be of use to determine the pharmacological properties of an angiotensin analog. In vivo, the effect of Ang(1-7) analogue on blood pressure reduction can be measured effectively after intravenous injection of the analog.

Ang(1-7) receptor agonistic activity is preferably defined as being capable of dilating isolated aorta rings that are pre-contracted with phenylephrine. In a particular aspect, there is provided a pharmaceutical composition comprising a 4,7-cyclised angiotensin analog of the invention, or a pharmaceutically acceptable salt or complexes thereof, and a pharmaceutically acceptable carrier, wherein said analog displays a vasodilating effect that is at least 1.2 times stronger as compared to naturally occurring Ang(1-7) as determined using isolated aorta rings preconstricted by incubation with $10^{7.5}$ M phenylephrine.

As will be understood, any known or yet to be discovered therapeutic or prophylactic use of naturally occurring Ang(1-7) will benefit from the present finding that a more stable analog can be prepared which has an Ang(1-7)-like activity. Useful applications of an Ang(1-7) analog (i.e. a 4,7-cyclized peptide having Ang(1-7) receptor agonistic activity) provided herein include treatment of hypertension and treatment of unwanted trachea constriction. Other useful applications are tissue repair, protection of bone marrow against cytostatica, antitumor applications and anti-inflammatory applications.

In a specific aspect, the invention relates to the use of a 4,7-cyclized peptide analog having Ang(1-7) receptor agonistic activity to accelerate wound healing. As indicated above, both Ang(1-7) and Ang(1-8) are capable of inducing tissue repair. However, Ang(1-7) and analogs thereof are less potent than Ang(1-8) at inducing hypertension. Such analog advantageously forms the basis of compositions useful for accelerating wound healing, the compositions comprising at least one analog effective to accelerate wound healing. Preferably, the compositions are in the form of matrical or micellar solutions. The cyclic Ang(1-7) analog may be administered in conjunction with a wound dressing. Provided is a method for accelerating re-epithelialization of wound tissue in a mammal, comprising applying to said wound tissue an amount of a 4,7-cyclized peptide analog having Ang(1-7) receptor agonistic activity effective for said acceleration.

According to a method of the invention, a 4-7-cyclized Ang(1-7) analog in accordance with the present invention, such as an Ang(1-7) analog with a thioether-bridge between position 4 and position 7 having the amino acid sequence Asp-Arg-Val-Abu-Ile-His-Ala, Asp-Arg-Val-Ala-Ile-His-Abu or the amino acid sequence Asp-Arg-Val-Ala-Ile-His-Ala, is applied to wound tissue in amounts sufficient to increase the healing rate of tissue. This analog can significantly accelerate the rate of healing at nanomolar levels in vivo. For any given active agent, the optimum concentration for a given formulation may readily be determined empirically. In general, an amount of active agent suitable for use in accordance with the present invention ranges from about 0.0001 μg to about 10 mg per kilogram body weight.

The analogs of the invention may be applied in a variety of solutions. Suitable solutions for use in accordance with the present invention are sterile, dissolve sufficient amounts of the peptide, and are not harmful to wound tissue.

Any type of application means may be employed which permits the influx of the active analog into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc). Methods for the production of these formulations with the analogs of the present invention are apparent to those of ordinary skill in the art. The particular concentration of active agent employed is not critical, as the tissue-repairing effect may be observed even when the analogs are present in nanomolar quantities. Preferably, a matrical or micellar solution is employed with the active angiotensin analog present in a concentration of at least 30 micrograms per milliliter. A particular matrical solution which has been used to advantage in the described examples is a semi-solid polyethylene glycol polymer sold under the trademark Hydron by Hydro Med Sciences, New Brunswick, N.J. Another preferred solution is a micellar solution sold under the trade name Pluronics F108 by BASF, Ludwigshafen, Germany. Under room temperature conditions, this solution is a liquid, but when applied to warm tissue the solution forms a gel which permits the infusion of active agent into the wound tissue for a period of several days. Other preferred formulations include carboxymethyl cellulose preparations (as used in the example herein), crystalloid preparations (e.g., saline, Ringer's lactate solution, phosphate-buffered saline, etc.), viscoelastics, polyethylene glycols, polypropylene glycols and wound dressings (e.g., bandages, etc.). The solution may be applied topically to surface wound tissue in the treatment of ulcers, lesions, injuries, diabetic ulcers, burns, trauma, stasis ulcers, periodontil conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active cyclic analog prior to closing the surgical site in order to accelerate internal capillary perfusion and healing. In addition, the rate of localized healing may be increased by the subdermal administration of active agent by injection or otherwise.

A further specific application of a cyclic Ang(1-7) receptor agonist according to the invention relates to preventing restenosis. It has been shown that Ang(1-7) receptor agonists can be used to preventing restenosis after vascular stent implantation by delivering them to the treatment site (see e.g. WO2006047289). Another useful application of a stable, 4,7-cyclised analog of the invention having Ang(1-7) receptor agonist activity therefore relates to suppression of vascular smooth muscle cell proliferation by delivering to the treatment site one or more agonists of the angiotensin(1-7) receptor. For example, the present invention provides a drug-eluting medical device, in particular a vascular stent, with a coating of cyclised angiotensin(1-7) analog-containing controlled-release polymer. Additionally the present invention provides the use of at least one 4,7-cyclized angiotensin analog having Ang-(1-7) receptor agonist in the manufacture of a medicament for treating impaired vascular endothelial cell function in a mammal, wherein said medicament is released from a surface of an implantable medical device. For example, provided is a vascular stent provided with a 4,7 cyclic Ang(1-7) analog having the amino acid sequence Asp-Arg-Val-Abu-Ile-His-Ala, Asp-Arg-Val-Ala-Ile-His-Abu or the amino acid sequence Asp-Arg-Val-Ala-Ile-His-Ala.

Also provided herein is the use of an angiotensin analog according to the present teachings having Ang(1-8) receptor antagonistic activity or a pharmaceutically acceptable salt or complexes thereof for the manufacture of a medicament for the treatment of a disease involving unwanted vasoconstriction. In one embodiment, the Ang(1-8) antagonist is a 4,7-cyclised Ang(1-7) analog as provided herein. In another embodiment, the Ang(1-8) antagonist is a 4,7-cyclised Ang (1-8) analog having an aliphatic residue at position 8 (preferably Ile) as provided herein. There are several diseases wherein unwanted vasoconstriction or unwanted constriction of the trachea occurs. For example, the invention provides the use of a [$Cyc^{4-7}$] analog having AngII antagonistic activity for the treatment of hypertension or heart failure. Another example is the use of 4,7 cyclised Ang(1-7) or an antagonistic 4,7 cyclised angiotensin(1-8) for the treatment of asthma or other cases of unwanted constriction of the trachea.

The AngII antagonists are also of value in the management of acute and chronic congestive heart failure, in the treatment of secondary hyperaldosteronism, primary and secondary pulmonary hyperaldosteronism, primary and secondary pulmonary hypertension, renal failure, renal vascular hypertension, ocular hypertension and impaired retinal blood flow, and in the management of vascular disorders such as migraine or Raynaud's disease. The application of the analogs of this invention for these and similar disorders will be apparent to those skilled in the art.

In the management of hypertension and other clinical conditions, the analogs of this invention may be utilized in compositions such as tablets, capsules or elixirs for oral administration, suppositories for rectal administration, sterile solutions or suspensions for parenteral or intramuscular administration, and the like. The peptide may also be administered via dry or liquid inhalation sprays into the lung. This route of administration is of particular interest for bronchi dilation. However, it is also suitable for systemic delivery of the peptide. (reviewed by Gonda, J Aerosol Medicine 19; 47-53 (2006)).

The analogs according to the invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The peptides according to the invention as well as pharmaceutically acceptable salt and complexes thereof are used for pharmacological purposes in the form of conventional pharmaceutical compositions. The term "pharmaceutically acceptable complexes" of the peptides according to the invention is used herein to refer to complex compounds formed with certain, for instance organic materials, endowing the peptides with a retarded activity. Typical representatives of these compounds are gelatines, carboxymethylcelluloses, alginic acid esters, poly(fluoroethinephosphates), amino acid polymers or other polymers and copolymers. As pharmaceutically acceptable salts the conventional, pharmaceutically acceptable acid addition salts, e.g., acetates are used.

The pharmaceutical compositions contain the compounds according to the invention in admixture with organic or inorganic carriers suitable for enteral or parenteral administration. Thus pharmaceutical compositions may be formulated as solid lyophilizates, in which various inert compounds not reacting with peptides, e.g., hydrocarbons can be used as carriers. When the pharmaceutical compositions are formulated as dilute or concentrated suspensions or emulsions, they contain also various preserving agents and stabilizing agents.

Pharmaceutical compositions containing an analog according to the invention which has Ang(1-8) receptor antagonistic or Ang(1-7) receptor agonistic activity may be used for differentiated detection of renal hypertensions as well as for the treatment of every syndrome caused by an increased renal blood pressure.

The compounds of this invention can also be administered in combination with other antihypertensives such as alpha-methyldopa, and/or diuretics such as hydrochlorothiazide, and/or angiotensin converting enzyme inhibitors such as enalapril, and/or calcium channel blockers such as nifedipine and/or AngII receptor antagonists (AT1 or AT2-receptor antagonists). [$Cyc^{4-7}$]Ang(1-7) can also be applied in combination with Ang(1-8) antagonists. This is consequent to the fact that different receptors are involved. Ang(1-8) acts on AT1 or AT2 receptors, whereas Ang(1-7) acts on MAS receptor. Typically, the individual daily dosages for these combinations can range from about one-fifth of the minimally recommended clinical dosages to the maximum recommended levels for the entities when they are given singly. These dose ranges can be adjusted on a unit basis as necessary to permit divided daily dosage and, and as noted above, the dose will vary depending on the nature and severity of the disease, weight of the patient, special diets and other factors. Typically, these combinations can be formulated into pharmaceutical compositions as discussed below.

About 1 to 100 mg of an analog or a mixture of analogs or a physiologically acceptable salt thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like;

a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the analog in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The Ang(1-8) receptor antagonistic analogs of this invention, e.g. 4,7-cyclised Ang(1-7) or the 4,7-cyclised Ang(1-8) Phe8Ile, are also useful to treat elevated intraocular pressure and can be administered to patients in need of such treatment with typical pharmaceutical formulations such as tablets, capsules, injectables, as well as topical ocular formulations in the form of solutions, ointments, inserts, gels, and the like. Pharmaceutical formulations prepared to treat intraocular pressure would typically contain about 0.9% to 15% by weight, preferably 0.5% to 2% by weight, of a compound of this invention.

Another aspect of the invention relates to the use of stabilized Ang analogs of the invention for stimulating or activating young cells, for example bone marrow cells, cells involved in tissue repair and the like. It has been shown (see e.g. U.S. Pat. No. 6,011,015) that Ang(1-8) or analogs thereof having Ang(1-8) receptor agonistic activity can be used for promoting fertilization of mammalian eggs. In this type of application of angiotensin analogs, Ang(1-7) appears to act as an Ang(1-8) receptor agonist, rather than as Ang(1-8) receptor antagonist. Accordingly, an agonistic 4,7-cyclised angiotensin analog of the invention can be used for promoting fertilization of mammalian eggs, especially human eggs. In particular, it provides the use of Ang(1-8) and Ang(1-7) analogs to improve sperm motility. The invention therefore also relates to a method of promoting in vitro fertilization of mammalian eggs, comprising adding a 4,7-cyclised Ang(1-8) or Ang(1-7) analog or a salt thereof to incubation medium containing oocytes and sperm.

A further application of cyclized analogs having Ang(1-8)-like activity relates to the transient stimulation of blood flow to a tumor or locally infected area by inducing vasoconstriction in the surrounding healthy tissue. This can be useful for targeted drug delivery at the affected site.

LEGENDS OF THE FIGURES

FIG. 1

Figure 1B:
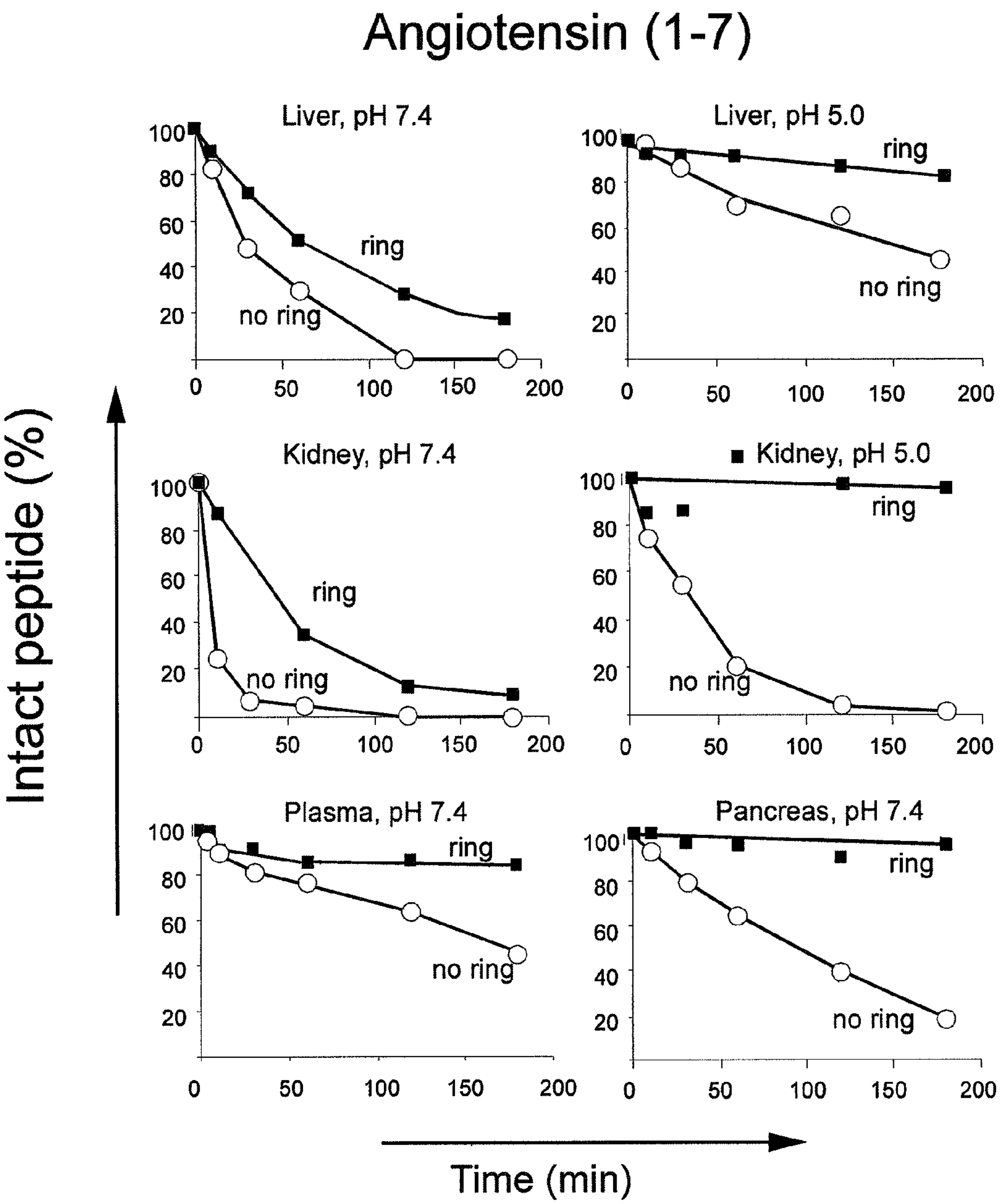

Comparison of native and thioether-ring-containing angiotensin with respect to protease resistance. FIG. 1A: native (open circles) and lanthionine containing angiotensin(1-8) (filled squares); FIG. 1B: native- (open circles) and lanthionine-containing (filled squares) angiotensin(1-7). Experimental details are mentioned in the text of example 1.

FIG. 2

Cyclized angiotensin(1-7) with thioether bridge between positions 4 and 7 is fully resistant against ACE.

A: Breakdown by 4 nM ACE of natural Ang(1-7) (open circles) or methyllanthionine-containing Ang(1-7) with the bridge between positions 4 and 7 (filled squares).

B: Formation of Ang(1-5) from natural Ang(1-7) (open circles) and from methyllanthionine-containing Ang(1-7) (filled squares) by incubation with 4 nM ACE.

C: Breakdown by 8 nM ACE of natural Ang(1-7) (open circles) or methyllanthionine-containing Ang(1-7) with the bridge between positions 4 and 7 (filled squares) or lanthionine-containing Ang(1-7) (open triangles).

D: Formation of Ang(1-5) from natural Ang(1-7) (open circles), from methyllanthionine-containing Ang(1-7) (filled squares) or from lanthionine-containing Ang(1-7) (open triangles) by incubation with 8 nM ACE. The experiment depicted in FIG. 2B corresponds to FIG. 2A; while FIG. 2D corresponds to FIG. 2C, respectively.

All points in FIG. A-D are the average of two measurements. Linked to the degradation of natural Ang(1-7) depicted in FIG. 2A and FIG. 2C, a breakdown product, natural Ang(1-5) was formed. This breakdown product was not formed in the case of thioether-ring-containing Ang(1-7). Experimental details are mentioned in the text of example 2.

FIG. 3

In vivo stability of thioether-ring-containing angiotensin (1-7) demonstrated by maldi TOF spectra of plasma from rat simultaneously infused with natural Ang(1-7) and methyllanthionine containing Ang(1-7).

Rats (Sprague Dawley) were infused during 2 hours at a speed of 1 mL/hour with a solution containing simultaneously two compounds: both 100 μM natural Ang(1-7) as well as 100 μM methyllanthionine-containing angiotensin(1-7) with the thioether bridge between positions 4 and 7. Methyllanthionine-containing angiotensin(1-7) was prepared using *L. lactis* expressing lantibiotic enzymes as described in example 1. Maldi TOF analyses were performed on plasma samples as described in example 3. Undiluted sample (upper spectrum, mass peak of 826.06 Da at the arrow) and 100-fold diluted sample (lower spectrum, mass peak of 826.47 Da at the arrow) both gave a peak of the right mass, i.e. corresponding to intact methyllanthionine-containing angiotensin(1-7) (Theoretical mass $M+H^+$ equals 825.9758). Natural angiotensin(1-7) was not detected at all. In a control experiment mixing natural angiotensin(1-7) ex vivo with rat plasma, allowed subsequent detection of natural angiotensin(1-7) (not shown). Experimental details are mentioned in the text of example 3.

FIG. 4

Cyclised Ang(1-7)-induced vasodilation of aortic rings.

Vasodilating effect of naturally occurring Ang(1-7) and an Ang(1-7) analog with a thioether bridging position 4 (D-Ala) and 7 (Ala) (a stereoisomer of compound I in FIG. 7), on aortic rings from Sprague Dawley rats.

Cross (x) represents a control; open circle: native Ang(1-7), filled square: thioether Ang(1-7). Each point represents the mean±SEM of data derived from 4 rats. Experimental details are mentioned in the text of example 4.

FIG. 5

Lowering of Ang(1-8)-induced trachea contraction by Ang (1-7) and cyclised Ang(1-7).

Contraction of trachea from guinea pigs induced by natural angiotensin(1-8) (cross, x), by natural angiotensin(1-8) after addition of natural angiotensin(1-7) (open circles) and by natural angiotensin(1-8) after addition of lanthionine-containing angiotensin(1-7) with the thioether between positions 4 and 7 (filled squares). Values are the means of 4 independent experiments. Experimental details are mentioned in the text of example 5.

FIG. 6A

Effect of natural Ang(1-7) and cyclized Ang(1-7) (cAng(1-7)) intravenous bolus injections on mean arterial blood pressure (MAP).

Saline pretreatment (white bars) and antagonist A799 pretreatment (black bars). Tested: 5-8 mice.

FIG. 6B

Effect of natural Ang(1-7) and cyclized Ang(1-7) (cAng(1-7)) intravenous bolus injections on recovery of mean arterial blood pressure (MAP) to pretreatment level. Saline pretreatment (white bars) and Ang(1-7) antagonist A799 pretreatment (black bars). *P<0.05 vs. Ang-(1-7) saline group. Tested: 5-8 mice.

FIG. 7

Lanthionine- and methyllanthionine analogs of angiotensin(1-7) with the thioether bridging positions 4 and 7 ([$Cyc^{4-7}$] Ang(1-7); compounds C, F and I), angiotensin(1-8) ([$Cyc^{4-7}$] Ang(1-8); compounds A, D and G) and angiotensin F8I angiotensin(1-8) ([$Cyc^{4-7}$] Ang(1-8)F8I; compounds B, E and H). Conventional one-letter code is used to indicate the amino acid at each position. Abu is 2-aminobutyric acid. Lanthionine is Ala-S-Ala, methyllanthionine is Abu-S-Ala or Ala-S-Abu. The sulfur atom in each structure may be oxidized once or twice.

The invention is further illustrated by the following examples.

EXAMPLE 1

Introduction of a Thioether Ring Between Position 4 to Position 7 Enhances the Proteolytic Resistance of Angiotensin(1-8) and Angiotensin(1-7)

Naturally occurring angiotensin(1-8) and angiotensin(1-7) are linear peptides with a short half-life as a result of rapid proteolytic breakdown. This example describes the introduction of a thioether-ring in Ang(1-7) and in Ang(1-8) between amino acids corresponding to positions 4 and 7 in Ang(1-8), i.e. $Tyr^4$ and $Pro^7$, resulting in [$Cyc^{4-7}$]Ang(1-7) having the sequence Asp-Arg-Val-Ala-Ile-His-Ala (compound I in FIG. 7) and [$Cyc^{4-7}$]Ang(1-8) having the sequence Asp-Arg-Val-Abu-Ile-His-Ala-Phe (compound A in FIG. 7), respectively.

Using homogenates of pig organs comprising several types of proteolytic enzymes, an enhanced resistance against enzymatic breakdown of [$Cyc^{4-7}$]Ang(1-8) and [$Cyc^{4-7}$]Ang(1-7) is demonstrated as compared to their non-cyclised, linear counterparts.

Experimental Procedure

Cyclized Ang(1-7) was produced both biologically and chemically, while cyclized Ang(1-8) was produced biologically.

Biological Production of [$Cyc^{4-7}$]Ang(1-8) and [$Cyc^{4-7}$] Ang(1-7)

Figure 7:
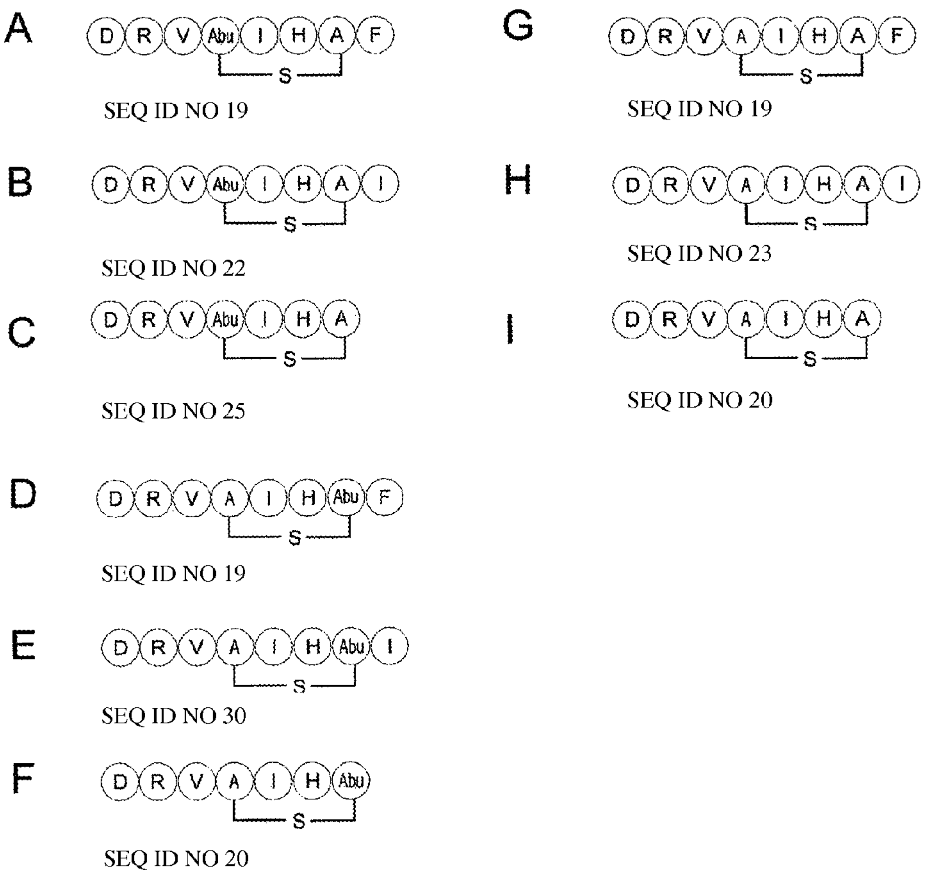

The production of cyclic angiotensin(1-8) and angiotensin (1-7) analogs containing a 4,7-(methyl)lanthionine thioether ring, [FIG. 7: compounds A, B, C, G, H, I] was started by designing oligonucleotides which encode the respective peptides. The amino acid at position 4 was Thr or Ser, while position 7 was Cys. The genetic code for the respective angiotensins was fused behind the coding sequence for the leader peptide from nisin and the N-terminal part of the nisin peptide (17-21 aa). When considering the peptide production level on the one hand and the extent of dehydration/thioether ring formation on the other, this fusion procedure proved to give the best results (instead of for instance direct fusion behind the leader peptide). A proteolytic cleavage site was introduced enabling liberation of the angiotensin from the fused nisin part (i.e. trypsin (Arg/Lys) or Factor Xa (IEGR).

The genetic code for the angiotensin-containing fusion peptide including Factor Xa site: Leader peptide-ITSISLCTPGCKTGALMIEGRDRV[T/S]IHC(F) was placed on a rolling circle plasmid, under the control of the nisin promoter and, in the presence of a second plasmid (theta replication) comprising the maturation genes nisB and nisC, as well as the transporter gene nisT under the same promoter, produced by the host organism *Lactococcus lactis*, strain NZ9000.

From an overnight (o/n) preculture in rich GM17 medium 1/50 of volume was transferred to MM medium (see Kluskens et al., 2005) supplied with 0.12 M MOPS (filter sterile). Immediate induction with nisin was performed, followed by growth o/n (16-18 h). Supernatant was obtained by centrifugation (10,000 rpm, 20 min, 8° C.) and subsequently filtered (0.2 μm). The supernatant was diluted (1:1) with wash buffer (50 mM lactic acid), and the 1 L in total was reduced in volume by running it over a 5 mL ion-exchange-chromatography column (HiTrap, Amersham) by 5 mL/min. After washing with 5 volumes of wash buffer, the peptide was eluted with elution buffer (50 mM lactic acid, 1 M NaCl). The peptide elutes between 5 and 10 ml in general.

The eluted peptide (e.g. 5 mL) was desalted using PD10 columns (Amersham) which typically results in 7 mL desalted peptide in solution. This was freeze-dried o/n, which in general results in an amount of approx. 10 mg dry weight per liter.

The fusion peptide was then enzymatically cleaved to release the peptide from leader-nisin fragment, using one of the enzymes mentioned earlier. Usually, 5 mg of dried fusion peptide was cleaved using 5-10 Units of enzyme (enterokinase, Factor Xa) or 5 ug Trypsin per ml reaction volume. Cleavage was carried out o/n at 23° C. (Factor Xa), or 4-6 h at 37° C. when trypsin was used. All reactions were carried out in a Tris buffer (100 mM Tris, pH 8.0, 100 mM NaCl, 2 mM $CaCl_2$).

Purification of the enzymatically cleaved peptide was performed by HPLC, using a reversed-phase column (C18). Sample was applied in a total volume of 200 μL, which contains 10% acetonitril (ACN)/0.1% TFA. With a gradient of 10 to 90% ACN the peptide was separated from the other peptide fragments. Sample, when pure, was then vacuum-dried and the protein concentration was determined using the Lowry method, and compared to a standard curve of BSA or a short, more similar peptide.

Ser/Thr dehydration was observed by a mass shift of −18 Da, when examined by Maldi-TOF mass spectrometry. In addition, ethanethiol additions were used, in which free dehydroresidues reacted with ethanethiol, resulting in a mass shift of +62 Da/dehydroresidue.

The presence of a thioether ring was proven by absence of chemical addition of CDAP (1-cyano-4-dimethylaminopyridinium tetrafluoroborate), which, in the case of absence of a ring, will react with available cysteine residues, that do not participate in thioether rings, and subsequently will result in a mass soft of +25 Da.

For the biological production of an Ang(1-8) analog ending with a Isoleucin at position 8 according to the above procedure, it is adantangeous to modity amino acids at positions 3 (Val) and/or 5 (Ile) in order to obtain correct dehydration and ring formation. Val3 found in the natural Ang(1-8) sequence may be replaced by Ile. Ile5 found in the natural Ang1-8)

sequence may be replaced by Val. Possible useful peptide sequences include DRITVHCI and DRITIHCI.

Chemical Production of [$Cyc^{4-7}$]Ang(1-7)

The following peptide was synthesized: H-Asp-Arg-Val-(D-)-Cys-Ile-His-Cys-OH. Thioether formation (lanthionine) was performed as described by Galande et al. ((2003) Biopolymers 71(5), 534-551). Briefly, 11.5 mg of a crude peptide preparation, which was approximately 50% pure, was dissolved in 10 mL milliQ that was saturated with $N_2$ (g). 5 droplets of 25% $NH_4OH$ were added and the solution was incubated in a 15 mL Greiner tube at 37° C. for 40 hours. The solution was dried in a speed-vac to remove the ammonia, and subsequently dissolved in milliQ containing 0.2% trifluoroacetic acid. The thioether peptide (Asp-Arg-Val-Ala-Ile-His-Ala; thioether bridge 4-7) was purified by reverse-phase HPLC on a C18 column with a gradient of milliQ (0.1% TFA) and acetonitril (0.1% TFA). The peak corresponding to the expected mass of 811 Da was collected and dried and dissolved in milliQ. The peptide concentration was determined by Lowry using BSA as standard. A total of 1.9 mg of thioether ring-containing peptide was obtained.

Natural (i.e. linear) Ang(1-8) peptide was obtained from Sigma (St Louis, Mo., USA) and natural Ang(1-7) from Bachem AG, Bubendorf, Switserland as ready-to-use compounds.

Measurements on the Proteolytic Resistance.

Angiotensin (wildtype or cyclised analogs, chemically produced [Cyc 4-7] Ang(1-7) or biologically produced [Cyc 4-7] Ang(1-8)) was added to homogenates of pig liver (0.2 μmol angiotensin/mg liver homogenate), pig kidney (0.2 μmol angiotensin/mg kidney homogenate), pig pancreas (0.8 μmol angiotensin/mg pancreas homogenate) or plasma (1 μmol angiotensin/ml) and incubated at 37° C., pH 7.4 or pH 5, for different time periods up to 30 hours. The enzymatic reaction was stopped by 100° C. for 5 min. The remaining amount of intact angiotensin was determined by RP-HPLC with C18-column, mobile phase gradient and 214 nm detection.

Results

Introduction of a thioether ring between position 4 and 7 resulted in a higher stability of angiotensin(1-8) and angiotensin(1-7) in all of the tested homogenates. Introducing the 4,7 thioether bridge in Ang(1-8) significantly increased its half-life in liver, kidney or pancreas homogenate at pH 7.4.

Ang(1-7) stability was measured at pH 7.4 as well as pH 5, the latter pH mimicking the lysosomal pH. At pH 7.4, the half-life of angiotensin(1-7) increased 2 (liver), 6 (kidney) and more than 18 (pancreas) fold by 4,7-cyclisation. At pH 5, in liver homogenate, ring introduction increased the half-life 5-fold. (Tables 1A, 1B; FIGS. 1A and 1B).

TABLE 1

| | | Degradation after 3 h (%) | | Half-life (min) | |
|---|---|---|---|---|---|
| homogenate | pH | linear | $Cyc^{4-7}$ | linear | $Cyc^{4-7}$ |
| A) Ang (1-8) | | | | | |
| Liver | 7.4 | 98 | 100 | 36 | 67 |
| Kidney | 7.4 | 100 | 100 | 1.5 | 7 |
| Pancreas | 7.4 | 70 | 21 | 104 | 483 |
| B) Ang (1-7) | | | | | |
| Liver | 7.4 | 100 | 82 | 32 | 68 |
| | 5.0 | 56 | 8 | 153 | 708 |

TABLE 1-continued

| | | Degradation after 3 h (%) | | Half-life (min) | |
|---|---|---|---|---|---|
| homogenate | pH | linear | $Cyc^{4-7}$ | linear | $Cyc^{4-7}$ |
| Pancreas | 7.4 | 81 | 4 | 81 | >24 hours |
| | 5.0 | 16 | 6 | ∞ | ∞ |
| Kidney | 7.4 | 100 | 91 | 5 | 32 |
| | 5.0 | 98 | 4 | 28 | >24 hours |
| Plasma | 7.4 | 55 | 15 | 166 | 926 |

Conclusion 4,7-cyclised analogs of Ang(1-7) and Ang(1-8) show a significantly enhanced resistance against enzymatic breakdown as compared to their natural, linear counterparts.

EXAMPLE 2

Thioether-ring-containing angiotensin is fully resistant against ACE

In vivo, ACE contributes strongly to breakdown of natural angiotensin(1-7) by cleavage of the peptide between the amino acids at positions 5 and 6. In view of the thioether bridge between positions 4 and 7 in the cyclised analogs of the invention, we hypothesised that the thioether bridge confers resistance against proteolytic degradation. In this example we investigated in vitro the resistance of angiotensin with and without thioether ring against angiotensin converting enzyme (ACE).

Methods.

Figure 2A:
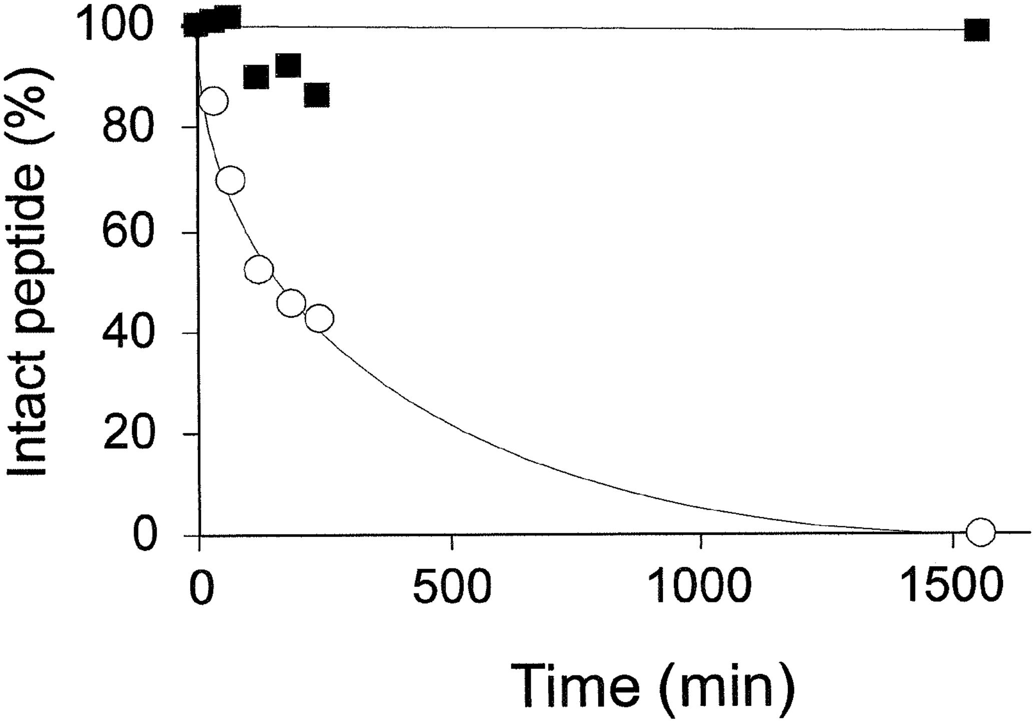
Figure 2B:
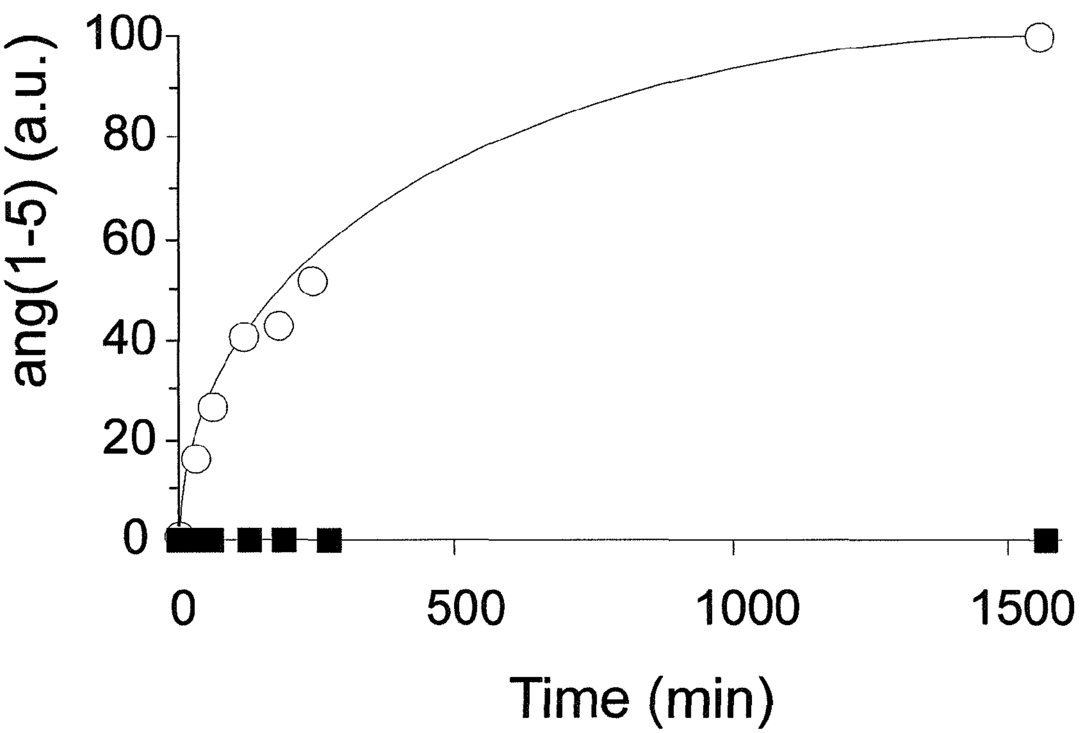
Figure 2C:
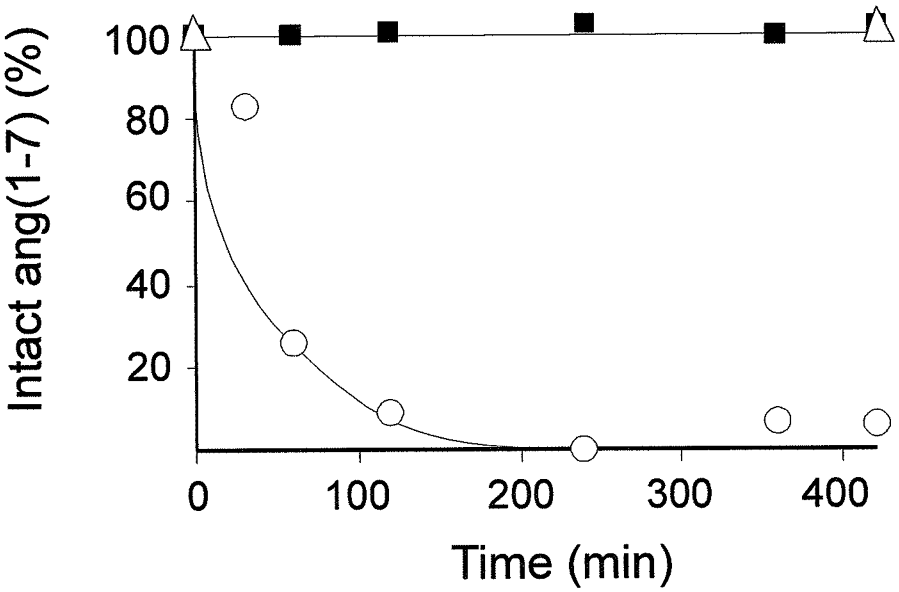
Figure 2D:
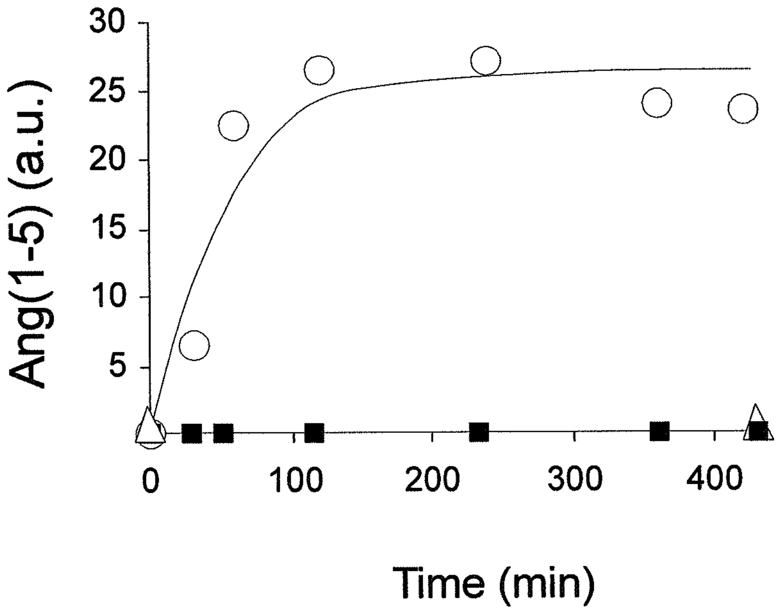

Angiotensin Converting Enzyme (ACE) from Porcine kidney, SIGMA, was used at 4 nM final concentration, FIGS. 2A and 2B, or at 8 nM final concentration, FIGS. 2C and 2D. Natural Ang(1-7) was purchased from Bachem. All experiments were performed in duplicate in a waterbath at 37° C., incubations were performed in a buffer containing 100 mM Tris-HCl, 300 mm NaCl, 10 μM Zn, pH 8.3. Thioether-ring-containing angiotensin was obtained by bacterial production using *L. lactis* containing the nisin modification and transporter enzymes, NisBTC. Natural angiotensin(1-7), lanthionine-containing angiotensin(1-7) and methyllanthionine-containing angiotensin(1-7) were each used at a concentration of 50 μM. Both the lanthionine and the methyllanthionine variant had the thioether bridge between positions 4 and 7. The reaction was stopped by 100° C. for 5 minutes and put on ice. Samples were centrifuged for 10 min at 14000 rpm at 4° C. and quantified by RP-HPLC. Identification of the HPLC peaks was performed using Maldi TOF mass spectrometry. All points are the average of two measurements.

Results.

FIG. 2A demonstrates that after 26 hour of incubation with 4 nM ACE, no degradation of the methyllanthionine variant has occurred (filled squares) while the natural angiotensin(1-7) is completely broken down (open circles). Breakdown of natural angiotensin(1-7) by ACE resulted in angiotensin(1-5) formation (FIG. 2B, open circles). Incubation of thioether angiotensin(1-7) with ACE did not lead to the appearance of Ang(1-5) (filled squares on the x-axis in FIGS. 2B and 2D). Even at a two fold higher ACE concentration, no breakdown of the thioether-bridged angiotensin analogs is observed (FIG. 2C, filled squares and open triangles) while natural angiotensin is rapidly broken down (FIG. 2C, open circles). Again, breakdown of natural angiotensin(1-7) coincides with the emergence of angiotensin(1-5), the primary breakdown product following ACE activity (FIG. 2D, open circles). No appearance of Ang(1-5) is observed after incubation of thioether angiotensin(1-7) with ACE (FIG. 2D) filled squares and open triages). These data demonstrate an exceptional resistance of the thioether-bridged angiotensin analog.

EXAMPLE 3

Thioether-ring-containing Ang(1-7) is highly stable in vivo

In this example we studied peptide stability during continuous ravenous infusion in the rat. It is demonstrated that a thioether ring in Ang(1-7) bridging positions 4 and 7 also confers proteolytic resistance in vivo, while the corresponding linear angiotensin without thioether ring is rapidly degraded.

Experimental

A male Sprague Dawley rat was kept under $O_2$/Isoflurane (1.5-2%) narcosis throughout the study. A jugular vein catheter was applied and connected to a syringe containing 0.9% physiological salt solution. The syringe was mounted onto an infusion pump and the flow rate set to 1 mL/hour. In the meantime a carotic artery catheter was applied and connected to a syringe containing 0.9% physiological salt solution. The rat was than heparinized via an injection in the penis vein. After 30 minutes the infusion pump syringe was replaced with a syringe containing a mix of 100 μM native Ang(1-7) and 100 μM methyllanthionine-containing Ang(1-7) analog. The flow rate was set at 1 mL/hour. Blood was sampled via the carotic artery. The blood samples were centrifuged 5 minutes at 13.000 RPM at 4° C. to obtain plasma. 5 μL plasma was added to 45 μL MQ water. The mixture was boiled 5 min, then put on ice for 10 min. After this the mixture was centrifuged for 10 min at 14000 rpm in an Eppendorf centrifuge, after which the supernatant was dried in a speed vac, resuspended in a few μl and added to the Maldi target for Maldi TOF analysis.

Results

Figure 3:
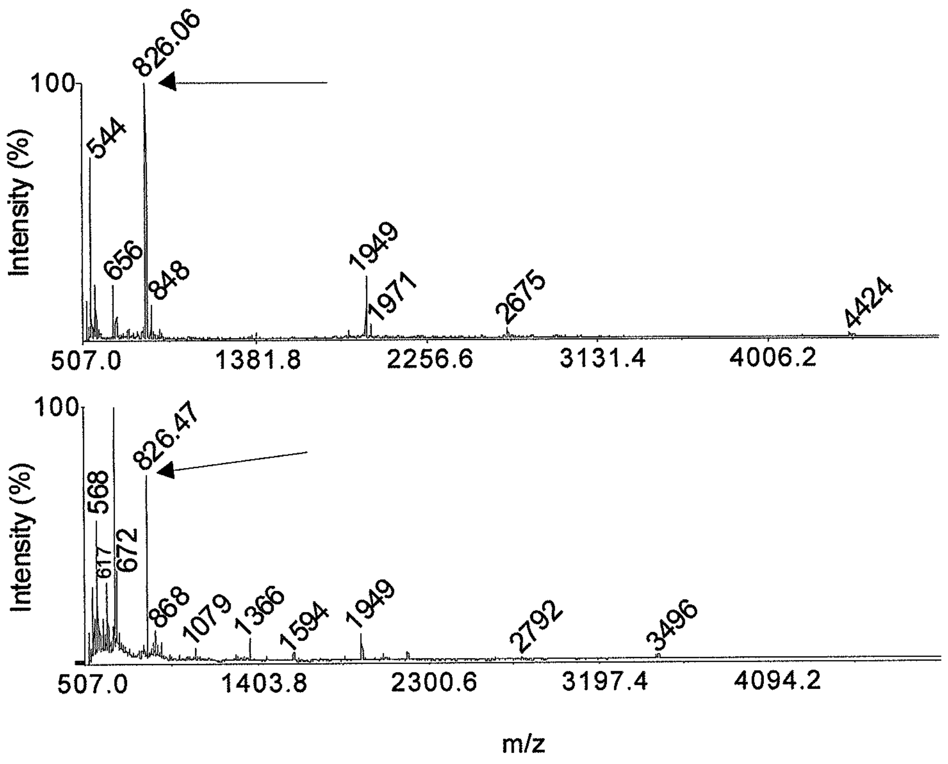

Thioether cyclised angiotensin was detected in the sample taken at 120 min. Undiluted sample (FIG. 3, upper spectrum, mass peak of 826.06 Da at the arrow) and 100-fold diluted sample (FIG. 3, lower spectrum, mass peak of 826.47 Da at the arrow) both gave a peak of the right mass, i.e. corresponding to intact methyllanthionine-containing angiotensin(1-7). Theoretical mass $M+H^+$ equals 825.98. Natural angiotensin (1-7) was not detected at all. A control experiment in which natural angiotensin(1-7) was mixed ex vivo with rat plasma, allowed subsequent detection of natural angiotensin(1-7) (not shown). These data demonstrate that in vivo the thioether-bridged angiotensin(1-7) is very stable, while the natural angiotensin(1-7) is rapidly and completely broken down.

Conclusion

These data demonstrate a prolonged lifetime of the cyclised thioether Ang(1-7). The higher plasma levels provide the thioether peptide with a better bioavailability, and thus an increased therapeutic potential.

EXAMPLE 4

Thioether-Ring-Containing Angiotensin(1-7) More Effectively Causes Vasodilation than Natural Angiotensin(1-7)

This example demonstrates the Ang(1-7) agonistic activity of thioether-ring-containing angiotensin(1-7) with the ring from position 4 to 7. In endothelium intact aorta rings from Sprague Dawley rats that are precontracted with phenylephrine, thioether ring containing angiotensin(1-7) causes dilation in a concentration-dependent manner and more effectively than the natural angiotensin(1-7).

Experimental

Aortic rings of male Sprague Dawley rats were used for isometric measurements of contraction and vasodilation. The rings were kept under a isometric tension of 1.3 g or 13 mN at 37° C. in a Krebs solution (pH 7.5) containing (in mM): NaCl (117.50), KCl (5.6), $CaCl_2.2H_2O$ (2.52), $MgSO_4.7H_2O$ (1.18), $NaH_2PO_4.H_2O$ (1.28), $NaHCO_3$ (25), D-glucose.$H_2O$, which was continuously gassed with 5% $CO_2$ and 95% $O_2$. To test the vasodilative effects of Ang(1-7), the aortic rings of each rat were divided in 3 groups for triplicate assessment of responses to a PE ($10^{-7.5}$ M)-induced peak contraction during each of the following treatments: control ($H_2O$), cumulative thioether-ring-containing Ang(1-7) ($10^{-10}$-$10^{-6}$ M) and cumulative native Ang(1-7) ($10^{-10}$-$10^{-6}$ M).

Results

Figure 4:
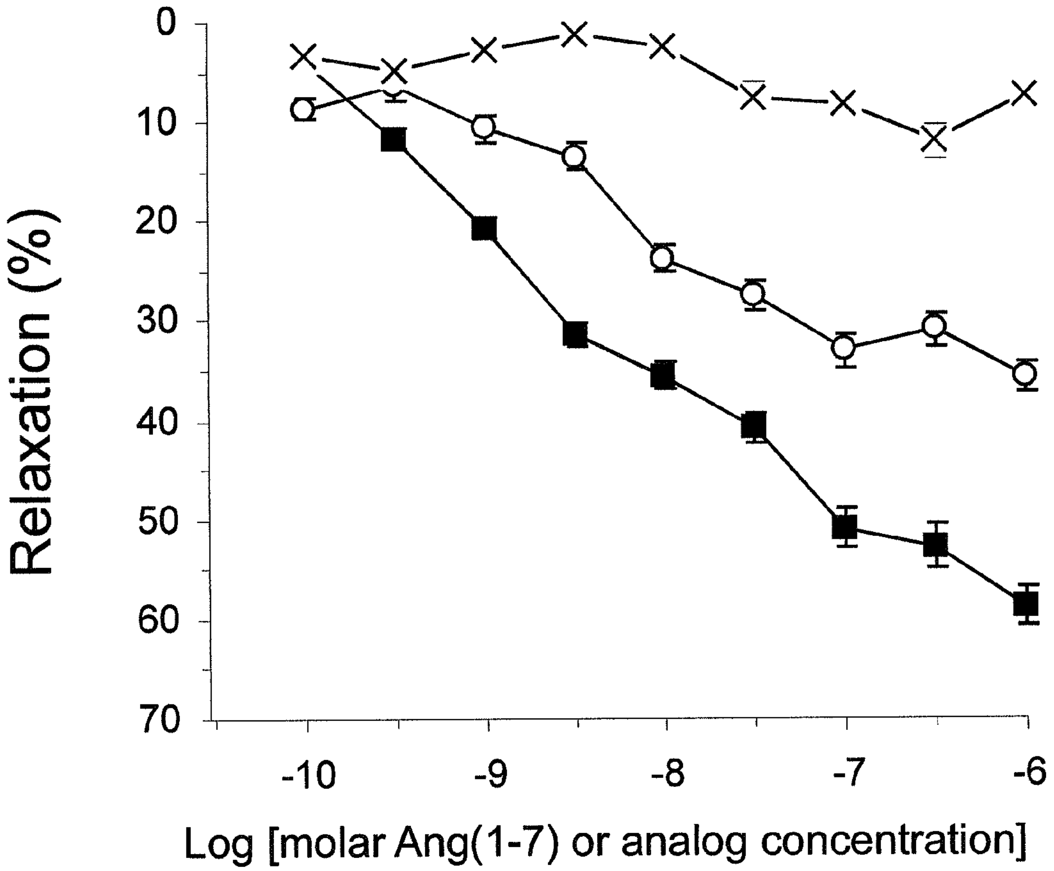

Both natural Ang(1-7) (FIG. 4, open circles) and thioether-containing-Ang(1-7), with lanthionine from position 4 to 7 (FIG. 4, filled squares), cause vasodilation of phenylephrine-contracted aorta. Negative controls without peptide are represented by crosses: x, FIG. 4. The vasodilating effect of the cyclized Ang(1-7) analog is significantly stronger, about two-fold more effective in amplitude, as compared to the natural Ang(1-7).

EXAMPLE 5

4,7-cyclised Ang(1-7) antagonizes Ang(1-8)-induced contraction of the trachea smooth muscle This example demonstrates that cyclised Ang(1-7) prevents Ang(1-8)-induced contraction of trachea rings. Similar to natural Ang(1-7), 4,7-cyclised Ang(1-7) antagonized Ang (1-8)-induced contraction of the trachea smooth muscle.

Experiment

Trachea rings of normal guinea-pigs were prepared for contraction measurements in isotonic organ bath set-up. The experiment was performed at 37° C. in a Krebs solution (pH 7.4) continuously gassed with 5% $CO_2$ and 95% $O_2$. First, maximal relaxation was established using isoprenaline $10^{-7}$ M, followed by wash-out (3 times) with Krebs solution until reaching stable tonus and then maximal contraction was determined using methacholine $10^{-4}$ M. After wash-out, cumulative concentrations ($10^{-10}$ up to $10^{-6}$ M) of native Ang(1-8) were given in the absence or presence of either linear Ang(1-7) or 4,7-cyclised Ang(1-7). The 4,7-cyclised Ang(1-7) was obtained either biologically or by sulfur extrusion as described in example 1. Cyclised peptides prepared either biologically or chemically gave very similar results. Ang(1-7) or its cyclised analog was added 20 minutes prior to the cumulative doses of Ang(1-8).

Results

Figure 5:
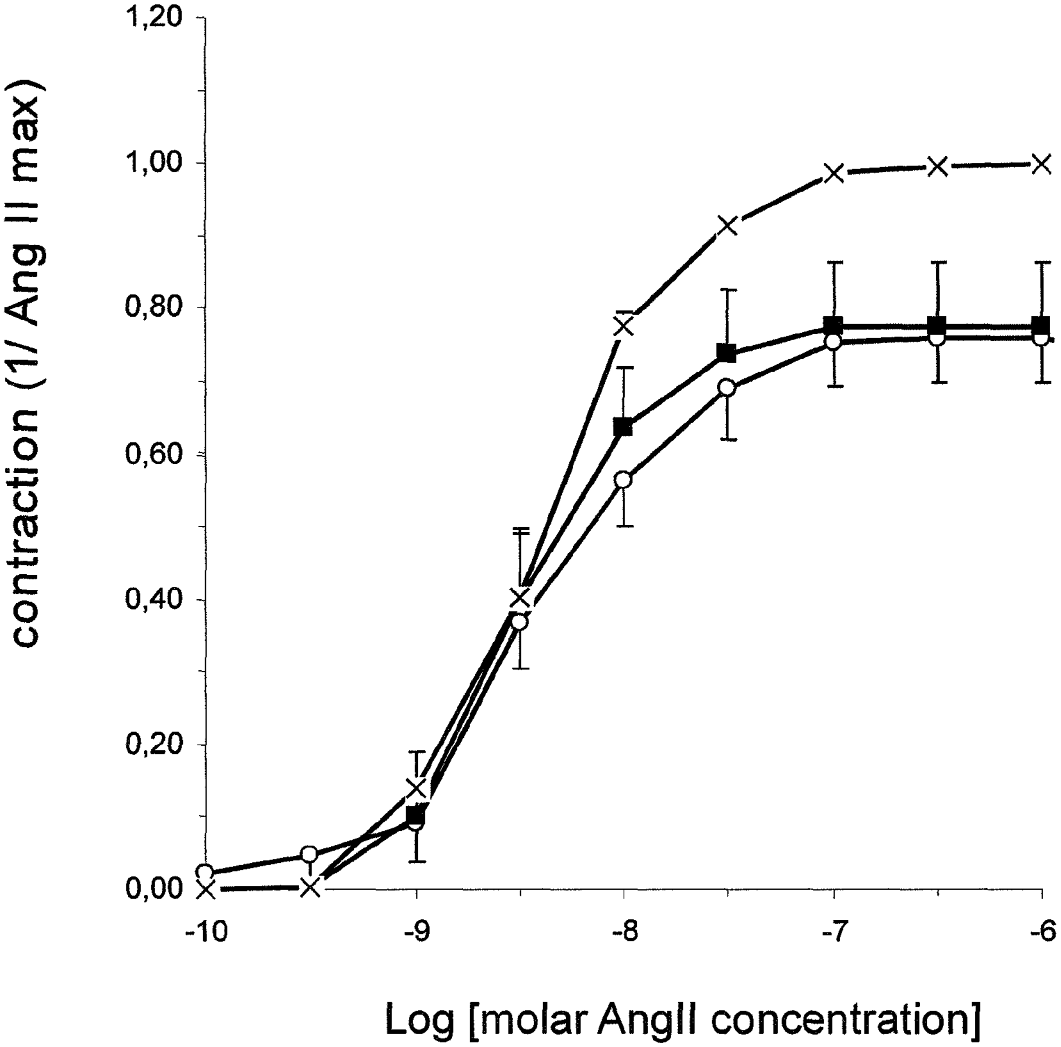

The 4,7-cycl-Ang(1-7) analog reduced the maximal contraction of trachea smooth muscle induced by Ang(1-8) by 24%. Linear Ang(1-7) caused a similar reduction (21% reduction, not significantly different from cyclized Ang(1-7)). (Table 2, FIG. 5).

TABLE 2

[$Cyc^{4-7}$]Ang(1-7) antagonizes contraction of the trachea smooth muscle induced by natural Ang(1-8).

| Angiotensin | mean contraction [%] | SD | SEM | P-values with respect to Ang(1-8) |
|---|---|---|---|---|
| Ang(1-8) | 24.21 | 4.58 | 1.53 | |
| Ang(1-7) + Ang(1-8) | 19.04 | 5.81 | 2.42 | 0.05 |
| [$Cyc^{4-7}$]Ang(1-7) + Ang(1-8) | 18.32 | 4.06 | 1.66 | 0.02 |

Conclusion

Introduction of a thioether ring between position 4 and 7 to stabilize Ang(1-7) yields a biologically active peptide analog which is an attractive analog for therapeutic purposes, for example for treatment of pulmonary diseases or disorders.

EXAMPLE 6

Thioether-ring-containing Ang(1-7) is more effective in lowering blood pressure than its linear counterpart In this example, we studied the effect of an intravenous bolus injection of cyclized Ang(1-7) on MAP (mean arterial blood pressure) in the anesthetized mouse. It demonstrates that cyclized Ang(1-7) lowers MAP more effectively than the natural, linear peptide. Additionally, the recovery of MAP back to normal is slower after cyclized Ang(1-7) administration.

Experimental

CD1 mice (35 to 40 g) remained under pentobarbital anesthesia throughout the study. Left jugular vein and right carotid artery were canulated for peptide injection and recording of the hemodynamic parameters, respectively. Five minutes after bolus injection of 100 μl of saline or 1 μmol/L A779, 0.6 μmol/L of either naturally occurring, linear Ang-(1-7) or 4,7-cyclized Ang-(1-7) were bolus injected via jugular vein in 100 μl volume. All peptides were suspended in saline. Blood pressure and heart rate were recorded for at least 15 minutes.

Results

Figure 6A:
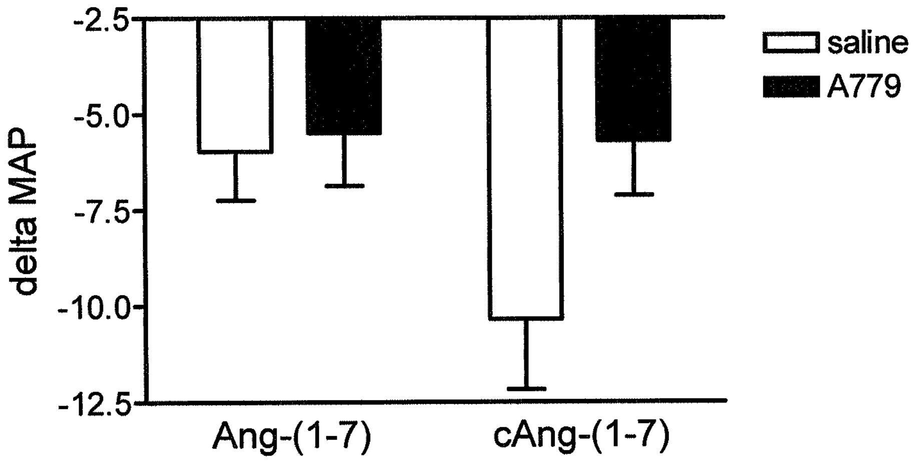
Figure 6B:
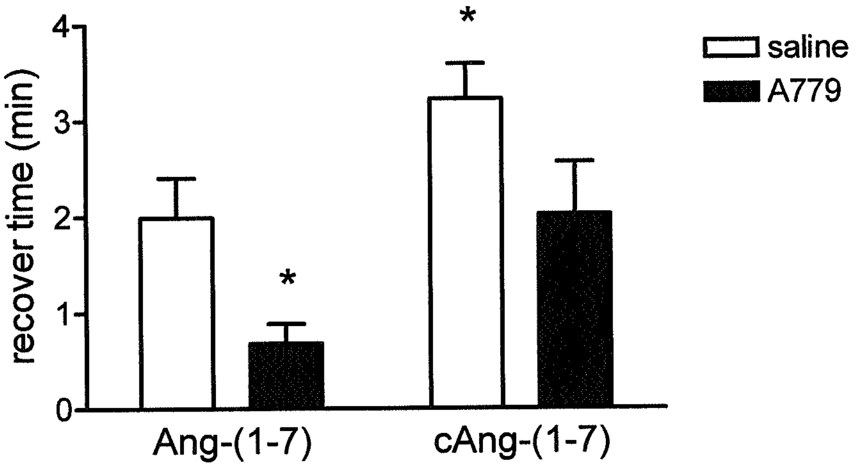

As shown in FIGS. 6A and B, an intravenous bolus injection of 0.06 μmol Ang(1-7) induced a temporary reduction of MAP in the anesthesized mouse.

The cyclized Ang(1-7), with a thio-ether ring bridging aminoacids 4 and 7, appeared approximately 2 fold more effective in lowering MAP when compared to the natural peptide. Looking at the recovery time of MAP, this shows that cyclized Ang(1-7) not only has a stronger effect on the degree of MAP reduction but also on the time-course of MAP reduction. After a bolus injection of cyclized Ang(1-7), MAP was back to normal after more than 3 min whereas after linear peptide injection the MAP recovery time was only 2 mm. Both improved effects of the cyclized peptide can be explained by its resistance against proteolytic degradation especially against degradation by ACE. However, an enhanced activity by improved receptor interaction of the conformationally constrained cyclized peptide as suggested by the aorta-contraction data (Example 4) may also play a role.

As for the linear peptide, the MAP effects of cyclized Ang(1-7) were effectively prevented by A779, a mas-receptor antagonist composed of Ang(1-7) in which the Pro7 is replaced by D-Ala. This proves that the MAP lowering activity of cyclized Ang(1-7) is a result of mas-receptor agonism.

Conclusion

These data demonstrate that, cyclization of Ang(1-7) results in a stronger and longer lasting lowering effect on MAP, via the mas-receptor. These in vivo data indicate that the cyclized compound has therapeutic value.

The invention claimed is:

1. A cyclic peptide analog of Angiotensin I (Ang(1-10)), Angiotensin II (Ang(1-8)), Angiotensin III (Ang(2-8)), Angiotensin IV (Ang(3-8)), Ang(1-7), Ang(2-7) or Ang(1-9), comprising a thioether-bridge linkage between the side chains of the amino acids corresponding to positions $Tyr^4$ and $Pro^7$ in naturally occurring Angiotensin, said analog consisting of the general formula $[Cyc^4\text{-}7]Xaa^{1\text{-}10}$, $[Cyc^{4\text{-}7}]Xaa^{1\text{-}9}$, $[Cyc^{4\text{-}7}]Xaa^{1\text{-}8}$, $[Cyc^{4\text{-}7}]Xaa^{1\text{-}7}$, $[Cyc^{4\text{-}7}]Xaa^{2\text{-}7}$, $[Cyc^{4\text{-}7}]Xaa^{2\text{-}8}$ or $[Cyc^{4\text{-}7}]Xaa^{3\text{-}8}$, wherein $Xaa^1$ is Asp $Xaa^2$ is Arg $Xaa^3$ is Ile or Val $Xaa^5$ is Ile or Val $Xaa^6$ is His $Xaa^8$ is Phe or Ile $Xaa^9$ is His $Xaa^{10}$ is Ile, Val or Leu, and wherein the thioether-bridge linkage between the amino acids corresponding to positions $Tyr^4$ and $Pro^7$ is of the general formula:

A)

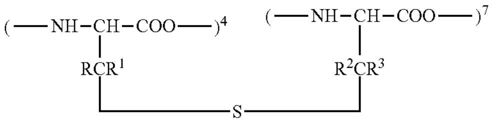

B)

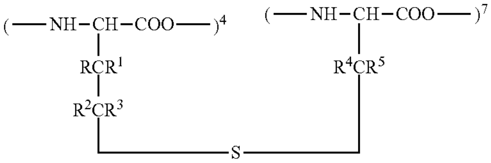

or

-continued

C)

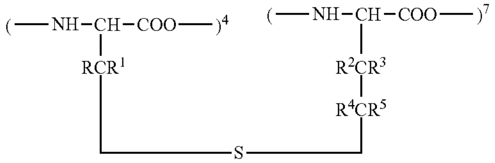

wherein R, $R^1$, $R^2$, $R^3$, $R^4$ and $R^5$ are independently selected from —H, a lower (e.g. $C_1$-$C_{10}$) alkyl and aralkyl group.

2. The analog according to claim 1, wherein said analog is Ang(1-7).

3. An implantable medical device, preferably a vascular stent, provided with a cyclic angiotensin analog according to claim 1 having Ang(1-7) receptor agonistic activity, or a pharmaceutically acceptable salt or complexes thereof.

4. A method for the treatment of a disease or disorder involving unwanted vasoconstriction, comprising administering to a subject in need thereof a therapeutically effective dose of a cyclic angiotensin analog according to claim 1 having Ang(1-8) receptor antagonistic activity and/or Ang(1-7) receptor agonistic activity, or a pharmaceutically acceptable salt or complexes thereof.

5. A method for the treatment of a disease or disorder involving unwanted trachea constriction, comprising administering to a subject in need thereof a therapeutically effective dose of a cyclic angiotensin analog according to claim 1 having Ang(1-8) receptor antagonistic activity and/or Ang(1-7) receptor agonistic activity, or a pharmaceutically acceptable salt or complexes thereof.

6. The method according to claim 4, wherein said angiotensin analog having Ang(1-8) antagonistic activity or Ang (1-7) agonistic activity is $[Cyc^{4\text{-}7}]$Ang(1-7).

7. The analog according to claim 1, wherein R, $R^1$, $R^2$, $R^3$, $R^4$ and $R^5$ are independently selected from H and $CH_3$.

8. The analog according to claim 1, wherein the thioether-bridge is of the formula A.

9. The analog according to claim 1, wherein $Xaa^4$ is a D-stereoisomer.

10. The analog according to claim 1, wherein $Xaa^7$ is an L-stereoisomer.

11. The analog according to claim 1, wherein $Xaa^1$ is Asp, $Xaa^2$ is Arg, $Xaa^3$ is Val, $Xaa^5$ is Ile, $Xaa^6$ is His, $Xaa^8$ is Phe, $Xaa^9$ is His, $Xaa^{10}$ is Leu.

12. The analog according to claim 1, selected from the group consisting of:

Asp-Arg-Val-Abu/Ala-Ile-His-Abu/Ala-Phe-His-Leu ($[Cyc^{4-7}]$Ang(1-10)),

Asp-Arg-Val-Abu/Ala-Ile-His-Abu/Ala-Phe-His ($[Cyc^{4-7}]$Ang(1-9)),

Asp-Arg-Val-Abu/Ala-Ile-His-Abu/Ala-Ile ($[Cyc^{4-7}]$Ang(1-8)F8I),

Arg-Val-Abu/Ala-Ile-His-Abu/Ala ($[Cyc^{4-7}]$Ang(2-7)),

-continued and

Asp-Arg-Val-Abu/Ala-Ile-His-Abu/Ala ($[Cyc^{4-7}]$Ang(1-7)), under the provision that the analog does not contain two Abu (2-aminobutyric acid) residues.

13. A pharmaceutical composition comprising a cyclic angiotensin analog according to claim 1, or a pharmaceutically acceptable salt or complexes thereof, and a pharmaceutically acceptable carrier.

14. The analog according to claim 8, wherein R, $R^1$, $R^2$ and $R^3$ are independently selected from H and $CH_3$.

15. The method according to claim 5, wherein said angiotensin analog having Ang(1-8) antagonistic activity or Ang (1-7) agonistic activity is $[Cyc^{4-7}]$Ang(1-7).

16. The method of claim 6, wherein said angiotensin analog is Asp-Arg-Val-Abu/Ala-Ile-His-Abu/Ala.

17. The method of claim 15, wherein said angiotensin analog is Asp-Arg-Val-Abu/Ala-Ile-His-Abu/Ala.

* * * * *